United States Patent [19]

Calverley et al.

[11] Patent Number: 5,401,731
[45] Date of Patent: Mar. 28, 1995

[54] VITAMIN D ANALOGUES

[75] Inventors: Martin J. Calverley, Herlev; Ernst T. Binderup, Tåstrup, both of Denmark

[73] Assignee: Leo Pharmaceutical Products Ltd. a/s (Løvens Kemiske Fabrik Productionsaktieselskab), Ballerup, Denmark

[21] Appl. No.: 113,522

[22] Filed: Aug. 30, 1993

Related U.S. Application Data

[63] Continuation of Ser. No. 793,417, Oct. 24, 1991, abandoned.

[30] Foreign Application Priority Data

Jun. 29, 1989 [GB] United Kingdom ............... 8914963

[51] Int. Cl.$^6$ ............................................. C07C 401/00
[52] U.S. Cl. ..................................... 514/167; 552/653
[58] Field of Search ..................... 552/653; 514/167

[56] References Cited

U.S. PATENT DOCUMENTS

| | | | |
|---|---|---|---|
| 4,069,321 | 1/1978 | Jones et al. | 552/653 |
| 4,188,345 | 2/1980 | DeLuca et al. | 552/653 |
| 4,195,027 | 3/1980 | DeLuca et al. | 552/653 |

OTHER PUBLICATIONS

WO A1 8404527, Nov. 22, 1984, p. 26, Claim 22.
Andrews et al, J. Org. Chem., 51:4819–4828, 1986.
Kutner et al, J. Org. Chem., 53:3450–3457, 1988.
J. Org. Chem. vol. 51, 1986 D. R. Andrews et al: "Synthesis of 25-Hydroxy-and 1, 25-Dihydroxyvitamin D3 from Vitamin D2 (Calciferol)", see p. 4819–p. 4828, 1986.
J. Org. Chem., vol. 53, 1988 A. Kutner et al.: "Novel Convergent Synthesis of Side-Chain-Modified Analogues of 1, 25-Dihydroxycholecalciferol and 1,25-Dihydroxyergocalciferol", see p. 3450–p. 3457, 1988.

*Primary Examiner*—Johann Richter
*Assistant Examiner*—Kimberly J. Kestler
*Attorney, Agent, or Firm*—Cushman Darby & Cushman

[57] ABSTRACT

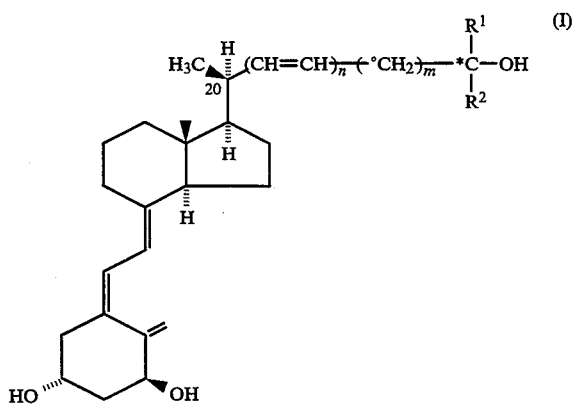

The present invention relates to compounds of formula (I), in which formula, n is 0 or 1, m is 0 or an integer from 1–7, $R^1$ and $R^2$ (which may be the same or different) stand for hydrogen or $C_1$-$C_8$-hydrocarbyl, or, taken together with the carbon bearing the hydroxyl group (starred in formula I), $R^1$ and $R^2$ can form a saturated or unsaturated $C_3$-$C_8$ carbocyclic ring. In addition, $R^1$ and/or $R^2$ and/or one of the m carbons designated by the "°" may be optionally substituted with a hydroxyl group or one or more chlorine or fluorine atom(s); and finally one of the carbons designated "°" may optionally be substituted by one or two $C_1$-$C_2$ alkyl group(s); and derivatives of the compounds of formula I in which one or more hydroxy have been transformed into —O-acyl or —O-glycosyl or phosphate ester groups; such masked groups being hydrolyzable in vivo. The present compounds find use in both the human and veterinary practice in the treatment and prophylaxis of autoimmune diseases (including diabetes mellitus), hypertension, ache, alopecia, skin ageing, imbalance in the imune system, inflammatory diseases such as rheumatoid arthritis and asthma as well as diseases characterized by abnormal cell differentiation and/or cell proliferation, such as e.g. psoriasis and cancer.

7 Claims, No Drawings

VITAMIN D ANALOGUES

This is a continuation of application Ser. No. 07/793,417, filed on Oct. 24, 1991, now abandoned.

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of a number of disease states including diabetes mellitus, hypertension, acne, alopecia, skin ageing, imbalance in the immune system, inflammatory diseases such as rheumatoid arthritis and asthma as well as diseases characterized by abnormal cell differentiation and/or cell proliferation such as e.g., psoriasis and cancer.

The compounds of the invention constitute a novel class of vitamin D analogues and are represented by the general formula I

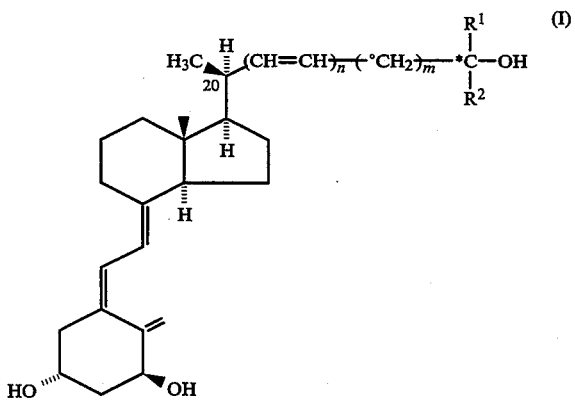

in which formula (and also throughout the remainder of this disclosure), n is 0 or 1, m is 0 or an integer from 1–7, $R^1$ and $R^2$ (which may be the same or different) stand for hydrogen or $C_1$–$C_8$-hydrocarbyl, or, taken together with the carbon bearing the hydroxyl group (starred in formula I), $R^1$ and $R^2$ can form a saturated or unsaturated $C_3$–$C_8$ carbocyclic ring. In addition, $R^1$ and/or $R^2$ and/or one of the m carbons designated by the "°" may be optionally substituted with a hydroxyl group or one or more chlorine or fluorine atom(s); and finally one of the carbons designated "°" may optionally be substituted by one or two $C_1$–$C_2$ alkyl group(s).

In the context of this invention, the expression hydrocarbyl radical indicates the residue after removal of a hydrogen atom from a straight, branched or cyclic saturated or unsaturated hydrocarbon.

Examples of $R^1$ and $R^2$ when taken separately include (apart from hydrogen), but are not limited to, methyl, trifluoromethyl, ethyl, vinyl, normal-, iso- and cyclopropyl, and 1-methylvinyl.

Examples of $R^1$ and $R^2$ when taken together include di-, tri-, tetra- and penta-methylene.

As can be seen from formula I, depending on the meanings of $R^1$, $R^2$, and n, the compounds of the invention include diastereoisomeric forms (e.g. E or Z configuration of a side chain double bond; R or S configuration at the starred carbon-atom). The invention covers all these diastereoisomers in pure form and also mixtures of diastereoisomers. It should be noted, however, that our investigations indicate a notable difference in activity between the stereoisomeric forms. In addition, derivatives of I in which one or more of the hydroxy groups are masked as groups which can be reconverted to hydroxy groups in vivo are also within the scope of the invention ("bioreversible derivatives or pro-drugs of I").

The term "bioreversible derivatives or prodrugs of I" includes, but is not limited to, derivatives of the compounds of formula I in which one or more hydroxy groups have been transformed into —O-acyl or —O-glycosyl or phosphate ester groups, such masked groups being hydrolyzable in vivo.

Also within the scope of this disclosure is another type of prodrug of I in which the hydroxyl group at the starred carbon atom is replaced by a hydrogen atom. These compounds are relatively inactive in vitro, but are converted to active compounds of formula I by enzymatic hydroxylation after administration to the patient.

It has recently been shown that $1\alpha,25$-dihydroxyvitamin $D_3$ ($1,25(OH)_2D_3$) influences the effects and/or production of interleukins (Immunol. Lett. 17, 361–366 (1988)), indicating the potential use of this compound in the treatment of diseases characterized by a dysfunction of the immune system, e.g. autoimmune diseases, host versus graft reactions, and rejection of transplants or other conditions characterized by an abnormal interleukin-1 production, e.g. inflammatory diseases such as rheumatoid arthritis and asthma.

It has also been shown that $1,25(OH)_2D_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of $1,25(OH)_2D_3$, or its pro-drug $1\alpha$-OH-$D_3$, for the treatment of hypertension (Lind, L. et al, Acta Med. Scand. 222, 423–427 (1987)) and diabetes mellitus (Inomata, S. et al, Bone Mineral 1, 187–192 (1986)) has been suggested. Another indication for $1,25(OH)_2D_3$ is suggested by the recent observation of an association between hereditary vitamin D resistance and alopecia: treatment with $1,25(OH)_2D_3$ may promote hair growth (Lancet, March 4, 1989, p. 478). Also, the fact that topical application of $1,25(OH)_2D_3$ reduces the size of sebaceous glands in the ears of male Syrian hamsters suggests that this compound might be useful for the treatment of acne (Malloy, V. L. et al., the Tricontinental Meeting for Investigative Dermatology, Washington, 1989). Finally, as thickening of the skin is observed in rats treated topically with $1,25(OH)_2D_3$, this compound may be useful for treatment or prevention of skin ageing.

However, the therapeutic possibilities in such indications of $1,25(OH)_2D_3$ are severely limited by the well known potent effect of this hormone on calcium metabolism; elevated blood concentrations will rapidly give rise to hypercalcemia. Thus, this compound and its potent synthetic analogues are not completely satisfatory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

Thus, the vitamin $D_3$ analogue, MC 903, containing a 22,23-double bond, a 24-hydroxy group and in which the carbon atoms 25,26 and 27 are incorporated in a three membered ring, is a potent inducer of cell differentiation and inhibitor of cell proliferation which shows only moderate activity on calcium metabolism in vivo (Binderup, L. and Bramm, E., Biochemical Pharmacology 37, 889–895 (1988)). However, this selectivity is not paralleled by in vitro studies, which show that MC 903 binds equally well as $1,25(OH)_2D_3$ to the intestinal vitamin D receptor. It may therefore be that the low in vivo activity on calcium metabolism of MC 903 is due to a rapid metabolism of the compound, thus limiting the potential of this compound for systemic use.

24-Homo-1,25-dihydroxyvitamin $D_3$ and 26-homo-1,25-dihydroxyvitamin $D_3$ (together with their 22,23-didehydroanalogues) (Ostrem, V. K.; Tanaka, Y.; Prahl, J.; DeLuca, H. F.; and Ikekawa, N.; Proc. Natl. Acad. Sci. USA 84, 2610–14 (1987)) have been claimed to have the same binding affinity as $1,25(OH)_2D_3$ to both the rat and chicken intestinal receptor and the receptor in a human myeloid leukemia cell line (HL-60), and yet to be 10-fold more potent than $1,25(OH)_2D_3$ in inducing differentiation of HL-60 cells in vitro. In vivo, these compounds are respectively "significantly less potent" and "more potent" than $1,25(OH)_2D_3$ in calcium metabolism assessments.

26,27-Dimethyl-1$\alpha$,25-dihydroxyvitamin $D_3$ has been synthesized, but the published information regarding its biological acitivities is contradictory. (Sai, H.; Takatsuto, S.; Hara, N.; and Ikekawa, N.; Chem. Pharm. Bull. 33, 878–881 (1985) and Ikekawa, N.; Eguchi, T.; Hara, N.; Takatsuto, S.; Honda, A.; Mori, Y.; and Otomo, S.; Chem. Pharm. Bull. 35, 4362–4365 (1987)). The closely related 26,27-diethyl-1$\alpha$,25-dihydroxyvitamin $D_3$ is also reported by these authors; in this case as having "almost no vitamin D activity" (i.e. calcium metabolism effects) while being 10-fold more potent than $1,25(OH)_2D_3$ in inducing cell differentiation.

The fact that there are only small structural differences between the above compounds indicates that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the observation that receptor binding affinities in vitro are not always paralleled by in vivo studies, probably reflecting a pharmacokinetic difference between the compounds.

The compounds of the present invention differ structurally from all vitamin D analogues which have been reported to have potent effects on cell differentiation/proliferation in the configuration of the methyl group at carbon-20. This "unnatural" configuration present in the compounds I has surprisingly been found to have a profound and advantageous biological significance. Thus a particular compound of formula I, when compared to the corresponding compound containing the "natural" C-20 configuration (methyl and hydrogen radicals exchanged), is observed to show one or more of the following advantages:
(a) more potent effects on cell differentiation/proliferation;

(b) a greater selectivity in favour of the potent effects on cell differentiation/proliferation contra the effects on calcium metabolism;

(c) more potent effects on the production and action of interleukins;

(d) a greater selectivity in favour of the effects on interleukin production and action contra the effects on calcium metabolism.

The compounds of the invention are therefore especially suited for both local and systemic treatment and prophylaxis of human and veterinary disorders which are characterized by 1) abnormal cell proliferation and/or cell differentiation, such as certain dermatological disorders including psoriasis and certain cancer forms, 2) an imbalance in the immune system, e.g in autoimmune diseases, including diabetes mellitus, host versus graft reaction, and rejection of transplants; and additionally for the treatment of inflammatory diseases, such as rheumatoid arthritis and asthma. Acne, alopecia, skin ageing, including photo-ageing, and hypertension are other conditions which may be treated with the compounds of the invention.

The present compounds may be used in combination with other pharmaceuticals. In the prevention of graft rejection and graft versus host reaction, a treatment with the present compounds may advantageously be combined with e.g. a cyclosporin treatment.

Compounds I can be prepared from the vitamin D-derived aldehyde 1j; a synthesis of which has been reported [M. J. Calverley, Tetrahedron 43, 4609 (1987)], optionally via the compounds 2j, 3j or 4j (Scheme 1), or from the compounds 1k, 2k, 3k or 4k, which may be obtained by triplet-sensitized photoisomerization of the corresponding compound j. Schemes 2 to 6 illustrate reactions for the conversion of these key intermediates to compounds I in which n, m, $R^1$ and $R^2$ have various meanings.

In Schemes 1-6, the following abbreviation is used:

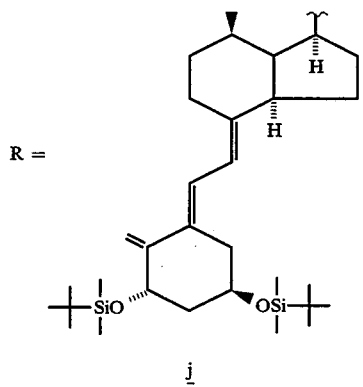

or

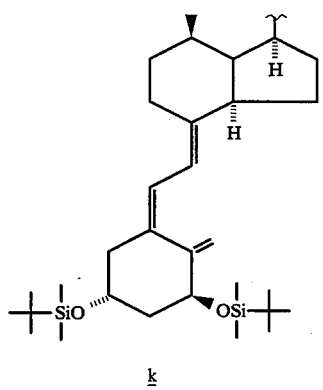

k

In the Notes to Schemes 1–7, appropriate aqueous work-up steps are implicit. For explanation of the expression "side chain fragment," see following text.

Scheme 1 -continued

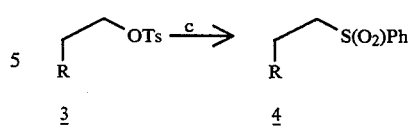

Notes to Scheme 1

R = j ⟶ R = k at any stage: hν-anthracene(toluene or CH₂Cl₂ containing Et₃N).

a. $\underline{1}$ ⟶ $\underline{2}$:(i)Ph₃⊕P—⊖CHCO₂Me(toluene)(gives compound $\underline{5}$ of Scheme 2); (ii)i-Bu₂AlH(THF)(gives compound III, $R^1=R^2=H$, of Scheme 2(compound 111));(iii) pyridinium dichromate(CH₂Cl₂);

b. (i)NaBH₄(EtOH—THF);(ii)TsCl-pyridine(CH₂Cl₂);

c. (i)PhS⊖K⊕(THF—DMF); (ii)H₂O₂—NaWO₄(MeCO₂Et—EtOH—H₂O).

Scheme 2

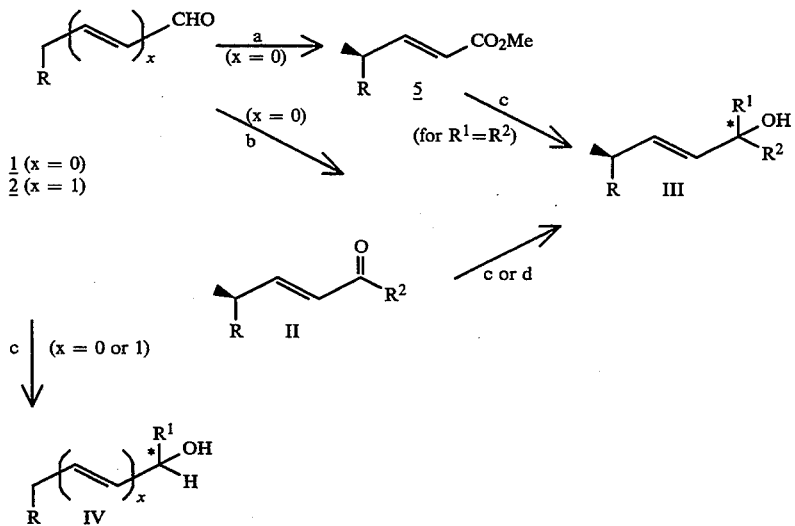

Notes to Scheme 2 a. Ph₃⊕P—⊖CHCO₂Me(toluene);

b. Metallated derivative, anion or ylide (C') from side chain fragment C(anhydrous solvent or phase transfer conditions);

c. R¹MgBr(R¹MgI) or R¹Li(THF);

d. NaBH₄—CeCl₃(THF—MeOH)(for R¹=H).

Scheme 1

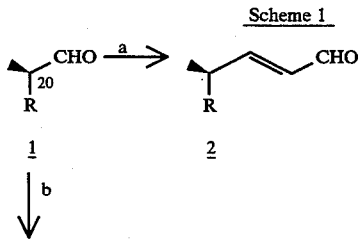

Scheme 3

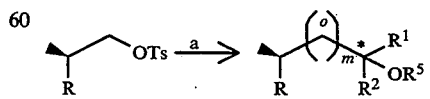

Note to Scheme 3 a. Grignard reagent (A') [derived from side chain fragment A (y = m − 2)] in the presence of Li₂CuCl₄(THF).

Scheme 3

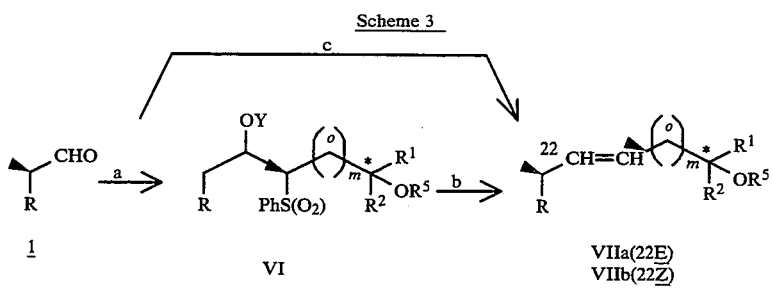

Note to Scheme 4 a. (i)Metallated derivative (B') of side chain fragment B (y = m)(THF);(ii)Optional derivatisation of the intermediate alkoxide (Y = M) or the isolated Y = H compound, e.g. with benzoyl chloride;

b. Reductive elimination mediated by e.g.Na—Hg[for Y = H, MeC(O)—, PhC(O)— or MeS(O$_2$)—];

c. Metallated derivative, anion or ylide (W') from side chain fragment W.

Scheme 5

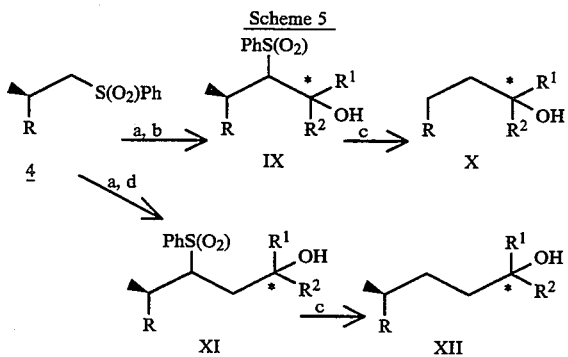

Notes to Scheme 5
a. LiN(Pr$^i$)$_2$(THF);
b. R$^1$C(O)R$^2$(THF);
c. Na—Hg(MeOH—EtOAc—Na$_2$HPO$_4$);
d. CH$_2$C(R$^1$)(R$^2$)(THF).
$\quad \backslash_O|$

Scheme 6

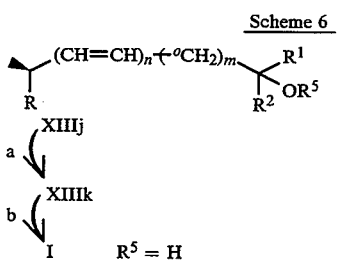

Notes to Scheme 6
R$^5$ = H or alcohol protective group
a. anthracene-hν(toluene or CH$_2$Cl$_2$ containing Et$_3$N);
b. (i) n-Bu$_4$N$^+$F$^-$(THF) or HF(MeCN—H$_2$O);
   (ii) any necessary reaction (sequence) for deprotecting OR$^5$—OH.

Compounds XIII correspond to the compounds of the type III, IV, V, VII, X or XII described in Schemes 2–5, and appear as these in Table 3 and the Preparations.

A key step in the syntheses as described is the reaction with an intermediate (of type A', B', W' or C') which is obtained by treatment of a side chain fragment of type A, B, W or C respectively) either by conversion to an organometallic agent or to an ylide, as appropriate.

All these types of reactions are well known in the art of carbon-carbon bond formation in synthetic organic chemistry, and have in fact been applied in syntheses of other vitamin D-type compounds.

In general, the side chain fragments have the structure:

$$Z—(^oCH_2)_y—C(R^1)(R^2)—OR^5 \quad \text{(Types A, B and W)}$$
$$Z—C(O)—R^2 \quad \text{(type C)}$$

with the following meanings (the following standard abbreviations are used throughout this disclosure: Bu=-butyl; Et=ethyl; Hep=heptyl; Me=methyl; Ph=phenyl; Pr=propyl; THP=tetrahydro-4H-pyran-2-yl; THF=tetrahydrofuran; Ts=p-toluenesulphonyl; DMF=N,N-dimethylformamide):

For type A, Z=X—$^o$CH$_2$—, where X is Cl, Br or I, and corresponding A' has Z=XMg—$^o$CH$_2$—.

For type B, Z=PhS(O$_2$)—CH$_2$—, and the corresponding B' has Z=PhS(O$_2$)—CHM—, where M=metal, e.g. Li.

For types C and W, Z=Ph$_3$P$^+$—CH$_2$— or Z=Q$_2$P(O)—CH$_2$—, where O=methoxy, ethoxy or phenyl, and the corresponding C' (W') has Z=Ph$_3$P$^+$—CH$^-$— or Q$_2$P(O)—CHM— (M=metal e.g. Li or metal equivalent, e.g. Bu$_4$N).

R$^5$ is optionally hydrogen or an alcohol protective group such as tri(loweralkyl)silyl or THP. In the case where R$^5$=H in A, B, or W, then R$^5$=M (M=metal, e.g. XMg or Li) in the derived A', B' or W'.

The syntheses of the particular fragments of types A and B can be varied greatly, but solely for the purpose of exemplification, the syntheses of the specific compounds shown in Table 1 using the routes summarized in Scheme 7 are described in the Preparations. It should be noted that the fragments of type B, with y, R$^1$ and R$^2$ corresponding to exemplified type A compounds, but which are not exemplified themselves,.are readily obtained from he corresponding described intermediates by analogous reactions. Fragments of type C or C' are known compounds or readily available as described for example in international patent application No. PCT/DK86/00081, international filing date 14th July, 1986, Publication No. WO 87/00834. Some Examples are listed in Table 2.

Some of these side chain fragments are converted (see Preparations and Examples) to the appropriate compounds I via the intermediates indicated in the Schemes. Parallel reactions can be used to convert other side chain fragments to the corresponding compounds I.

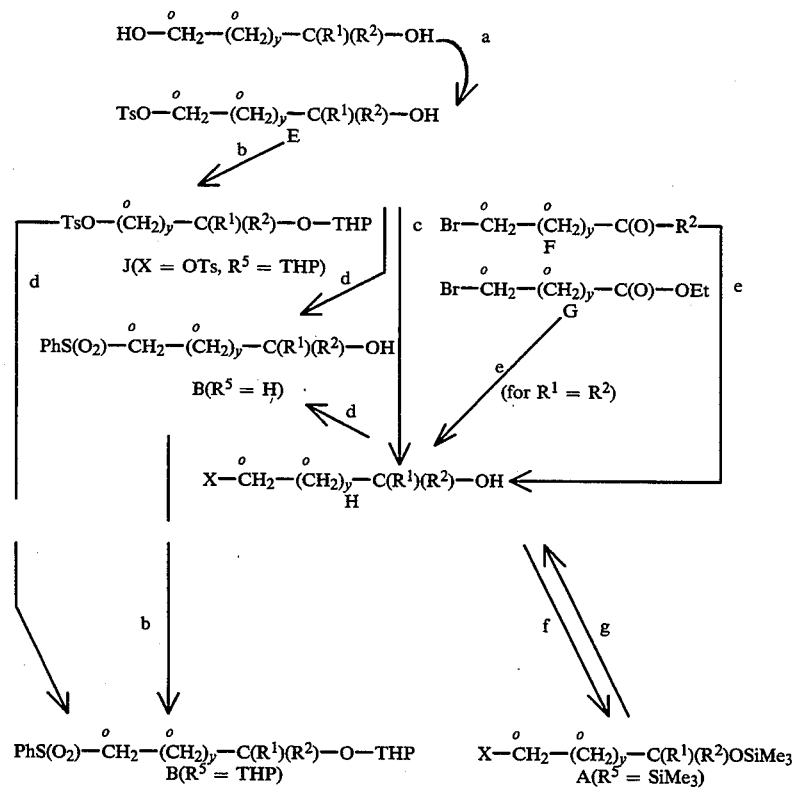

Scheme 7

Notes to Scheme 7 a. TsCl-base; b. dihydropyran-acid; c. LiBr(for X = Br) or

NaI(for X = I); d. (i)PhSH-base, (ii)$H_2O_2$—$NaWO_4$;

e. Grignard reagent $R^1$MgBr or $R^1$MgI; f. $Me_3$SiCl-base; g. MeOH-acid;

TABLE 1

Some Specific Side Chain Fragments (Types A and B
[Z—($°CH_2$)$_y$—C($R^1$)($R^2$)$OR^5$]

| Compound Number+ | Type* | y | $R^1$ | $R^2$ | $R^5$ | Z |
|---|---|---|---|---|---|---|
| 6++ | A | 1 | Me | H | SiMe$_3$ | ICH$_2$ |
| 7** | A | 1 | H | Me | SiMe$_3$ | ICH$_2$ |
| 8** | A | 1 | H | Hep | SiMe$_3$ | ICH$_2$ |
| 9 | A | 1 | Me | Me | SiMe$_3$ | BrCH$_2$ |
| 10 | A | 1 | —(CH$_2$)$_2$— | | SiMe$_3$ | BrCH$_2$ |
| 11 | A | 1 | —(CH$_2$)$_4$— | | SiMe$_3$ | BrCH$_2$ |
| 13 | A | 2 | —(CH$_2$)$_2$— | | SiMe$_3$ | BrCH$_2$ |
| 14 | A | 2 | Et | Et | SiMe$_3$ | BrCH$_2$ |
| 15 | A | 2 | Pr | Pr | SiMe$_3$ | BrCH$_2$ |
| 16 | A | 3 | Me | Me | SiMe$_3$ | BrCH$_2$ |
| 18 | A | 3 | Pr | Pr | SiMe$_3$ | BrCH$_2$ |
| 17 | A | 3 | Et | Et | SiMe$_3$ | BrCH$_2$ |
| 19 | A | 4 | Me | Me | SiMe$_3$ | BrCH$_2$ |
| 20 | A | 5 | Me | Me | SiMe$_3$ | BrCH$_2$ |
| 21 | B | 1 | Me | Me | H | PhS(O$_2$)CH$_2$ |
| 22 | B | 1 | —(CH$_2$)$_2$— | | THP | PhS(O$_2$)CH$_2$ |
| 23 | B | 2 | Et | Et | H | PhS(O$_2$)CH$_2$ |
| 24 | B | 3 | Me | Me | H | PhS(O$_2$)CH$_2$ |
| 25 | B | 4 | Me | Me | H | PhS(O$_2$)CH$_2$ |
| 26++ | A | 1 (CH(Me)) | Me | Me | SiMe$_3$ | BrCH$_2$ |
| 27** | A | 1 (CH(Me)) | Me | Me | SiMe$_3$ | BrCH$_2$ |
| 28++ | B | 1 (CH(Me)) | Me | Me | H | PhS(O$_2$)CH$_2$ |

TABLE 1-continued

Some Specific Side Chain Fragments (Types A and B
[Z—(°CH$_2$)$_y$—C(R$^1$)(R$^2$)OR$^5$]

| Compound Number+ | Type* | Formula ↓ y | R$^1$ | R$^2$ | R$^5$ | Z |
|---|---|---|---|---|---|---|
| 29** | B | 1 (CH(Me)) | Me | Me | H | PhS(O$_2$)CH$_2$ |

+As referred to in the Preparations
*See text
++S-Form
**R-Form
Unsubstituted CH$_2$ unless otherwise indicated by specifying an alternative meaning of "(°CH$_2$)".

TABLE 2

Some Specific Side Chain Fragments (Type C and C')[Z—C(O)R$^2$]

| Compound Number | R$^2$ | Z |
|---|---|---|
| 30 | ]—CHMe$_2$[ | Ph$_3$⊕PCH⊖ |
| 30a |  | (EtO)$_2$P(O)CH$_2$ |
| 31a  y = 1 | —CH(CH$_2$)$_y$CH$_2$ | Ph$_3$⊕PCH⊖ |
| 31b  y = 2 |  |  |
| 31c  y = 3 |  |  |
| 31d  y = 4 |  |  |
| 32 | —CCl—CH$_2$—CH$_2$ | Ph$_3$⊕PCH⊖ |
| 33 | —CF—CH$_2$—CH$_2$ | (EtO)$_2$P(O)CH$_2$ |
| 34 | —CMe$_3$ | Ph$_3$⊕PCH⊖ |
| 35 | —CHEt$_2$ | Ph$_3$⊕PCH⊖ |
| 36 | —CH(n-Pr)$_2$ | Ph$_3$⊕PCH⊖ |

For the synthesis of compounds I in which the starred carbon atom is chiral (R$^1$≠R$^2$), the compound D in Scheme 7 is conveniently used as the stereoisomer with largely or exclusively the required configuration, to give largely or exclusively the required diastereoisomer(s) of I.

Alternatively, the compound D may be used as the stereoisomer having the opposite configuration, and the configuration may be then inverted at a later stage in the synthesis.

In other cases where R$^1$≠R$^2$ in compounds I, the isomers in the corresponding intermediates XIII can be separated (e.g. by chromatography), and the configuration at the starred carbon atom can be inverted or equilibrated at this stage by application of standard reactions.

The synthesis of the prodrugs of compounds I which lack the side chain hydroxyl (at the starred carbon atom) may follow the routes of Schemes 3 and 4, Using the appropriate side chain fragment of structure Z—(°CH$_2$)$_y$—CH(R$^1$)(R$^2$). The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the disease state which is to be treated, the route of administration and the mammal under treatment. The compounds of the invention can be administered by the parenteral, intra-articular, enteral or topical routes. They are well absorbed when given enterally and this is the preferred form of administration in the treatment of systemic disorders.

Conveniently, the active ingredient comprises from 0.1-100 μg/g for topical formulations and 0.05-100 μg/g for oral and parenteral formulations.

By the term "dosage unit" is meant a unitary, i.e. a single dose which is capable of being administered to a patient as a physically and chemically stable unit dose comprising either the active material as such or a mixture of it with solid or liquid pharmaceutical diluents or carriers.

The formulations, both for veterinary and for human medical use, of the present invention comprise an active. ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including transdermal, subcutaneous, intramuscular and intravenous), intraarticular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100µ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$-$C_6$-alkyl hydrocarbons or halogenated $C_1$-$C_6$-alkyl hydrocarbons or mixtures thereof; chlorinated and flourinated $C_1$-$C_6$-alkyl hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.05-100 µg, preferably from 0.1-50 µg, of a compound of formula I are administered. In the topical treatment of dermatological disorders, ointments, creams or lotions containing from 0.1-100 µg/g, and preferably from 1-10 µg/g, of a compound of formula I are administered. The oral compositions are formulated, preferably as tablets, capsules, or drops, containing from 0.025-100 µg, preferably from 0.05-50 µg, of a compound of formula I, per dosage unit.

The invention will now be further described in the following non-limiting Preparations and Examples:

PREPARATIONS AND EXAMPLES

General

The exemplified compounds I are listed in Table 4. The intermediates of Schemes 1-6 referred to in the Preparations are to be identified by numbers with the corresponding formulae in Table 3. These are used to illustrate typical syntheses of the exemplified compounds I.

The compound of Example 19 (not listed in Table 4) corresponds to compound 122 in which the hydroxyl group at the starred carbon atom of formula I is replaced by a hydrogen atom.

For nuclear magnetic resonance spectra (300 MHz) chemical shift values ($\delta$) are quoted for deuteriochloroform solutions relative to internal tetramethylsilane ($\delta = 0$) or chloroform ($\delta = 7.25$). The value for a multipier, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

TABLE 3

| | Compounds of Schemes 2-6 which are Intermediates in the Preparation of Compounds I of Scheme 6 | | | | | | |
|---|---|---|---|---|---|---|---|
| Compound Number (R = j or k) | Type | Scheme | x | m ‡ | $R^1$ | $R^2$ | $R^5$ |
| 101j | II | 2 | — | — | — | .CHCH$_2$CH$_2$ | — |

TABLE 3-continued

Compounds of Schemes 2-6 which are Intermediates in the Preparation of Compounds I of Scheme 6

| Compound Number (R = j or k) | Type | Scheme | x | m‡ | R¹ | R² | R⁵ |
|---|---|---|---|---|---|---|---|
| 102j, 103j, 102k, 103k | III | 2, 2, 6, 6 | — | — | H | .CHCH₂CH₂ | — |
| 104j, 105j, 104k, 105k | IV | 2, 2, 6, 6 | 0 | — | .(CH₂)₂CMe₂<br>\|<br>OSiMe₃ | — | — |
| 106j, 106k | V | 3, 6 | — | 3 | Me | Me | SiMe₃ |
| 107j, 107k | V | 3, 6 | — | 4 | Et | Et | SiMe₃ |
| 108j, 108k | V | 3, 6 | — | 5 | Me | Me | SiMe₃ |
| 109j, 109k | VIIa | 4, 6 | — | 2 | Et | Et | H |
| 110j, 110k | VIIb | 4, 6 | — | 2 | Et | Et | H |
| 111j, 111k | III | 1,2, 6 | — | — | H | H | — |
| 112j, 113j | IV | 2 | 0 | — | Me | — | — |
| 112k, 113k | IV | 6 | 0 | — | Me | — | — |
| 114j, 115j, 114k, 115k | IV | 2, 2, 6, 6 | 0 | — | .(CH₂)₄CMe₂<br>\|<br>OSiMe₃ | — | — |
| 116j, 116k | VIIa | 4, 6 | — | [(S¹)—CH(Me)] | Me | Me | H |
| 117j, 117k | VIIb | 4, 6 | — | | | | |

TABLE 3-continued

Compounds of Schemes 2–6 which are Intermediates in the Preparation of Compounds I of Scheme 6

| Compound Number (R = j or k) | Type | Scheme x | m | $R^1$ | $R^2$ | $R^5$ |
|---|---|---|---|---|---|---|
| 118j<br>118k | VIIa | 4<br>6 | — | [($R^1$)—CH(Me)] | Me | Me | H |
| 119j<br>119k | VIIb | 4<br>6 | | | | |

Note as for Table 1
NB
(i) Where identical descriptions for two numbered compounds are given (e.g. 102j and 103j) the compounds are distinguished only in their configuration at the starred carbon atom. These configurations give rise to two series of compounds, referred to as "isomer A" and "isomer B" in the Preparations and Examples.
(ii) Where a hydroxyl group is present in $R^1$, $R^2$ or one of the "*" carbons of formula I, then this may optionally be protected in the corresponding intermediates (e.g. 104 and 105).

TABLE 4

Exemplified Compounds I

| Compound Number | m | n | $R^1$ | $R^2$ |
|---|---|---|---|---|
| 120<br>121 | 0 | 1* | H | —CHCH$_2$CH$_2$— |
| 122 | 3 | 0 | Me | Me |
| 123 | 4 | 0 | Et | Et |
| 124 | 2 | 1* | Et | Et |
| 125 | 2 | 1+ | Et | Et |
| 126 | 1 | 1* | H | H |
| 127<br>128 | 0 | 0 | Me | H |
| 129<br>130 | 0 | 0 | (CH$_2$)$_2$CMe$_2$<br>\|<br>OH | H |
| 131<br>132 | 0 | 0 | (CH$_2$)$_4$CMe$_2$<br>\|<br>OH | H |
| 133 | 5 | 0 | Me | Me |
| 134<br>135 | [($S^1$)—CH(Me)] | $\begin{bmatrix} 1* \\ 1+ \end{bmatrix}$ Me | Me | Me |
| 136<br>137 | [($R^1$)—CH(Me)] | $\begin{bmatrix} 1* \\ 1+ \end{bmatrix}$ Me | Me | Me |

Notes as for Table 3;
*22(E);
+22(Z) (The carbon in the side chain connected to C-20 apart from the methyl group is C-22)

Preparation 1

4-Bromo-2-methyl-2-trimethylsilyloxybutane (Compound 9)

To a stirred, ice-cooled solution of ethyl 3-bromopropionate (G, y=1) (15.0 ml) in dried ether (100 ml) was added dropwise over 1 hour a filtered solution of Grignard reagent, prepared from magnesium (10 g) and methyl iodide (25 ml) in dried ether (200 ml). After a further 30 minutes on the ice bath, the reaction mixture was allowed to warm to room temperature over 30 minutes before being poured onto a stirred, ice-cooled solution of ammonium chloride (30 g) in water (200 ml). After the vigorous reaction had subsided, the ether layer was separated, and the aqueous layer was extracted with more ether. The combined ether layers were washed consecutively with water and brine, dried, and concentrated in vacuo to give the crude intermediate carbinol H (y=1, $R^1$=$R^2$=Me) as a pale yellow oil. This Was dissolved in dichloromethane (130 ml) and triethylamine (40 ml) and 4-dimethylaminopyridine (0.2 g) added. The stirred solution was ice-cooled during the addition of trimethylsilyl chloride (27 ml) dropwise over 30 minutes. The reaction mixture was then stirred at room temperature for 2 hours before being partitioned between ether (500 ml) and water (500 ml). The ether layer was washed four times with water, once with brine, and dried. After removing the solvent in vacuo, the residue was distilled to give a product, b.p. 75°–77° C./11 mmHg. A portion (5 g) of the product was purified by chromatography (150 g silica gel; 1% ether in petroleum ether as eluant) and redistilled to give the pure bromide (9) as an oil, δ (300 MHz) 0.10 (9 H, s), 1.23 (6 H, s), 2.02 (2 H, m) and 3.44 (2 H, m).

Preparation 2

3-Hydroxy-3-methylbutyl phenyl sulphone (Compound 21)

To a solution of 4-bromo-2-methyl-2-trimethylsilyloxybutane (9) (12 g) in methanol (55 ml) at room temperature was added ethanolic hydrogen chloride (ca. 1M, 0.2 ml). After 10 minutes the solution was concentrated in vacuo (at room temperature) to constant weight. The residue was taken up in chloroform and reconcentrated to constant weight to give 4-bromo-2-methyl-2-butanol (H, y=1, $R^1$=$R^2$=Me) as a chromatographically homogenous oil. The product was dissolved in THF (10 ml) and added to a premixed, stirred solution of potassium tert-butoxide (3.7 g) and thiophenol (3.6 ml) in N,N-dimethylformamide (50 ml) at room temperature. After a few minutes a precipitate started forming, and after 30 minutes the mixture was partitioned between ethyl acetate (300 ml) and water (200 ml). The organic layer was washed consecutively with 2N sodium hydroxide solution, water and brine. Drying and concentration in vacuo gave 3-hydroxy-3-methylbutyl phenyl sulphide as a chromatographically homogenous oil. This was dissolved in methanol (60 ml), and to the stirred solution was added sodium hydrogen carbonate (4.7 g), aqueous sodium tungstate solution (2%, 5 ml) and hydrogen peroxide (100 vol, 11.8 ml). The initial exothermic reaction which ensued was checked by momentary ice-cooling. The reaction mixture was then-stirred at 50° C. for 1 hour. After cooling the mixture was partitioned between dichloromethane (200 ml) and water. The aqueous layer was extracted with more dichloromethane, and the combined dichloromethane layers were washed with water, brine, and dried. Concentration in vacuo gave a crude product which was purified by chromatography (150 g silica gel; ether as eluant) to give the sulphone (21) as a viscous oil, 6 (300 MHz) 1.22 (6H, s), 1.64 (1H, bs), 1.88 (2H, m), 3.25 (2H, m), 7.55–7.70 (3H, m), 7.93 (2H, m).

Preparation 3

4-Hydroxy-4-ethylhexyl phenylsulphone (Compound 23)

The compound was prepared using the procedure of Preparation 2, except using 6-bromo-3-methyl-3-trimethylsilyloxyhexane (compound 14) as starting material, via the corresponding intermediates 6-bromo-3-methyl-3-hexanol (H, y=2, $R^1=R^2=Et$) and 4-hydroxy-4-ethylhexyl phenyl sulphide. 23; 6 (300 MHz) 0.82 (6H, t, J 7.5), 1.31 (1H, s), 1.43 (4H, q, J 7.5), 1.48 (2H, m), 1.74 (2H, m), 3.13 (2H, m), 7.57 (2H, m), 7.66 (1H, m) and 7.92 (2H, m).

Preparation 4

Compound 26

The compound was prepared from 1-p-toluenesulphonyloxy-2(S), 3-dimethyl-3-hydroxybutane (J. Org. Chem. 53, 3457–3465 (1988)) by tosylate exchange with LiBr followed by trimethylsilylation using a procedure analogous to the relevant section of Preparation 5 of our international patent application No. PCT/DK89/00079, international filing date 7th April, 1989.

Preparation 5

Compound 27

The compound was prepared analogously to Compound 26 (Preparation 4), from 1-p-toluenesulphonyloxy-2(R),3-dimethyl-3-hydroxybutane. This compound was prepared analogously to the 2(S)-isomer as described in J. Org. Chem. 53, 3457–3465 (1988), but using methyl (S)-(+)-3-hydroxy-2-methylpropionate as starting material instead of the (R)-(−)-isomer.

Preparation 6

Compound 29

The compound was prepared analogously to Compound 28 as described in J. Org. Chem. 53, 3457–3465 (1988), but using methyl (S)-(+)-3-hydroxy-2-methylpropionate as starting material instead of the (R)-(−)-isomer. M.p. 67°–68° C., $[\alpha]_D=35°$ (c 1, CHCl$_3$).

All other compounds of Table 1, except compound 28 (prepared as described in J. Org. Chem. 53, 3457–3465 (1988)), were prepared as described in international patent application No. PCT/DK89/00079, international filing date 7th April, 1989.

As indicated in M. J. Calverley, Tetrahedron 43, 4609 (1987), Compound 1J was prepared by base-catalysed equilibration of its C-20 epimer and separated by chromatography (5% Et$_2$O in petroleum ether as eluant). The compound has now been obtained crystalline (from Et$_2$O-MeOH).

Preparation 7a

Compound 31b

The compound was prepared as described for the corresponding compound 31a [M. J. Calverley, Tetrahedron 43, 4609 (1987)] except using cyclobutyl methyl ketone instead of cyclopropyl methyl ketone. 31l: δ (300 MHz) 1.70–2.00 (2H, m), 2.05–2.35 (4H, m), 3.21 (1H, m), 3.66 (1H, d, J 26), 7.4–7.7 (15H, m).

Preparation 7b

Compound 32

The compound was prepared as described for the corresponding compound 31a [M. J. Calverley, Tetrahedron 43, 4609 (1987)] except using 1-chlorocyclopropyl methyl ketone instead of cyclopropyl methyl ketone. 32:6 (300 MHz) 1.11 and 1.57 ( each 2H, m ), 4.58 ( 1H, d, J 25 ), 7.4–7.7 ( 15H, m).

Preparation 8

Compound 33

This compound was prepared using a procedure analogous to that described for the preparation of the corresponding compound 30a (J. Org. Chem., 1982, 47, 2163), except using 1-fluorocyclopropyl methyl ketone as starting material. 33; b.p. 90°–93° C./0.2 mmHg, 6 (inter alia) 3.47 (1H, J 3.7 and 22.6).

Preparation 9

1(S),3(R)-bis-tert-butyldimethylsilyloxy-20(R)-hydroxymethyl-9,10-secopregna-5(E),7(E),10(19)-triene A stirred, ice-cooled solution of the aldehyde 1j (5 g) in THF (20 ml) and ethanol (70 ml) was treated with sodium borohydride (0.35 g). After 10 minutes the reaction mixture was partitioned between ethylacetate and water, and the organic layer was washed with brine and dried. Concentration in vacuo gave the title compound, δ (300 MHz) 0.05 (12H, bs), 0.56 (3H, s), 0.86 (9H, s), 0.89 (9H, s), 0.96 (3H, d, J 7), 1.1–2.1 (15H, m), 2.31 (1H, bd), 2.55 (1H, dd, J 14 and 5), 2.86 (1H, bd), 3.48 (1H, dd, J 10 and 7), 3.71 (1H, dd, J 11 and 4 ), 4.21 (1H, m), 4.52 (1H, m), 4.93 (1H, bs), 4.98 (1H, bs), 5.82 (1H, d, J 11.5), and 6.44 (1H, d, J 11.5).

Preparation 10

1(S),3(R)-bis-tert-butyldimethylsilyloxy-20(R)-p-toluenesulphonyloxymethyl-9,10-secopregna-5(E),7(E), 10(19)-triene (Compound 3j)

The compound from Preparation 9,1(S),3(R)-bis-tert-butyldimethylsilyloxy-20(R)-hydroxymethyl-9,10-secopregna-5(E),7(E),10(19)-triene (5 g) was dissolved in dichloromethane (25 ml) and pyridine (3 ml), and the solution was stirred and ice-cooled during the addition of p-toluenesulphonyl chloride (2.5 g). The reaction mixture was allowed to stand at 5° C. overnight before being partitioned between ethyl acetate and water. The organic layer was washed consecutively with saturated copper sulphate solution (twice), water, 5% sodium hydrogen carbonate solution, and brine, and then dried and concentrated in vacuo. The residue was purified by chromatography (200 silica gel; 5% ether in petroleum ether as eluant) to give title compound, δ (300 MHz) 0.035 (3H, s), 0.044 (3H, s), 0.051 (3H, s), 0.056 (3H, s), 0.45 (3H, s), 0.85 (9H, s), 0.88 (9H, s), 0.89 (3H, d, J 6), 1.15–2.05 (14H, m), 2.28 (1H, bd), 2.44 (3H, s), 2.52 (1H, dd, J 14 and 5), 2.84 (1H, bd), 3.81 (1H, m), 4.11 (1H, m), 4.20 (1H, m), 4.51 (1H, m), 4.93 (1H, bs), 4.97 (1H, bs), 5.79 (1H, d, J 11), 6.42 (1H, d, J 11), 7.33 (2H, bd) 7.78 (2H, bd).

Preparation 11

1(S),3(R)-bis-tert-butyldimethylsilyloxy-20(R)-formyl-9,10-secopregna-5(Z),7(E),10(19)-triene (Compound 1k)

The compound was prepared analogously to Procedure 4 (see below) in which the starting material was 1j. 5% Ether in petroleum ether was used as eluant. 1k $\neq$ (300 MHz) 0.05 (12H, bs), 0.52 (3H, s), 0.86 (18H, s), 1.03 (3H, d, J 6), 1.1–2.5 (16H, m), 2.82 (1H, bd), 4.17 (1H, m), 4.36 (1H, m ), 4.84 ( 1H, bd ), 5.16 ( 1H, m ), 6.00 and 6.20 ( each 1H, d, J 11), and 9.56 (1H, d, J 8).

Procedure 1a

Reaction of aldehyde 1 with stable ylide $C'(Z=Ph_3P^+—CH^-)$ to give II (Scheme 2)

A stirred mixture of 1 and a molar excess of C' in toluene (10 ml per gram 1) was heated under reflux under an $N_2$ atmosphere until a reasonable or complete conversion of was obtained (4 to 16 hours). After cooling, the mixture was filtered, and the filtrate concentrated and purified by chromatography (5–10% ether in petroleum ether for the examples of Table 2) to give II.

Compound 101j (obtained thus from 1j and 31a) is described in Tetrahedron 43, 4609 (1987).

Procedure 1b

Reaction of aldehyde 1 with C'(W')-formed in situ from side chain fragment C(W)

An equivalent amount of 1 (dissolved in THF) was added to an ice-cooled solution of C'(W') in THF [prepared by adding base (BuLi or NaH, 1 equivalent) to a solution of C or W (2 equivalents base for W with $R^5=H$)]. After stirring overnight, the reaction mixture was worked up (ether), and the residue purified by chromatography to give the compound II (from C) or VII (from W).

Preparation 12

Compounds 102j and 103j

Sodium borohydride (0.29 g) was added to an ice-cooled, stirred solution of 101j (2.5 g) in tetrahydrofuran (8 ml) and 0.4M $CeCl_3·7H_2O$ in ethanol (11.5 ml). Methanol (6 ml) was added over 10 minutes, and after stirring for a further 20 minutes the mixture was partitioned between ethyl acetate and water. The organic layer was washed with water, dried and concentrated in vacuo. The residue was purified by chromatography (silica gel; toluene:acetone 97:3 as eluant) to give the title compounds. The first eluted product was isomer A (102j); $\delta$ (100 MHz ) 0.06 ( 12H, s ), 0.53 ( 3H, s ), 0.13–0.68 (4H, m), 0.87 (9H, s ), 0.90 ( 9H, s), additionally 0.70–2.70 (21H, m), 2.85 (1H, m), 3.44 (1H, m), 4.20 (1H, m), 4.51 (1H, m), 4.95 (2H, m), 5.52 (2H, m), 5.80 (1H, d, J 12 and 6.45 (1H, d, J 12); $\lambda_{max}$ 270 nm ($\xi=24900$) (crystallized from methanol). The second eluted product was isomer B (103j). M.p. 104°–5° C. (from methanol); $\delta$ (100 MHz) 0.06 (12H, s), 0.53 (3H, s), 0.15–0.65 ( 4H, m ), 0.87 ( 9H, s ), 0.90 ( 9H, s ), additionally 0.67–2.70 (21H, m), 2.85 (1H, m), 3.40 (2H, m), 4.21 (1H, m), 4.52 (1H, m), 4.95 (2H, m), 5.50 (2H, m), 5.80 (1H, d, J 12 and 6.45 (1H, d, J 12); $\lambda_{max}$ 270 nm ($\xi=24500$).

Procedure 2

Reaction of aldehyde 1 or 2 with (a) $R^1MgBr$ ($R^1MgI$) or (b) $R^1Li$ to give IV (Scheme 2)

(a) An aliquot (2 ml) of the Grignard reagent obtained from $R^1Br$ ($R^1I$) (20 mmol) (in the event that $R^1$ contains a hydroxy group in the compound I, this may be protected for example as a trimethylsilyl ether for the reaction of Procedure 2. The unmasking of this hydroxyl then occurs during the reaction of Procedure 5), and magnesium (20 mmol) in dry THF (15 ml) was added dropwise to a stirred solution of 1 or 2 (1 mmol) in dry THF (5 ml) at 0° C. After 30 min., the reaction mixture was partitioned between water and ether, and the ether layer was washed with brine, dried and concentrated in vacuo. Purification of the residue by chromatography gave IV.

(b) The organo-lithium reagent (1.5M in ether or hexanes, 1 ml) was substituted for the aliquot of Grignard reagent in (a), running the reaction at −40° C. instead of 0° C.

Preparation 13

Compounds 104j and 105j

Using Procedure 2a, starting with compounds 9 and 1 j, and using 5% ethyl acetate in petroleum ether for the chromatography, the title compounds as were obtained as isomer A (less polar isomer) and B, respectively.

Procedure 2c

Conversion of tosylate 3 to V Scheme 3 )

This procedure is illustrated in Preparations 14 and 51.

Preparation 14

Compound 106j

The stirred Grignard reagent obtained from Compound 9 (5.0 g) and magnesium (0.53 g) in dry THF (15 ml) was treated at 0° C. with a solution of lithium chloride (68 mg) and anhydrous cupric chloride (108 mg) in dry THF (8 ml) followed by a solution of Compound 3j (1.0 g) in dry THF (5 ml). After 5 hours, the reaction mixture was partitioned between water and ether, and the ether layer was washed with brine, dried and concentrated in vacuo. Purification of the residue by chromatography (150 g silica gel, petroleum ether to 2% ether in petroleum ether as eluant) followed by crystallisation from ether-methanol gave the title compound $\delta$ (300 MHz) 0.05 (12H, bs), 0.09 (9H, s), 0.54 (3H, s), 0.85 (3H, d, J 6), 0.85 (9H, s), 0.89 (9H, s), 1.19 (6H, s), additionally 1.2–2.05 (20H, m), 2.30 (1H, bd), 2.55 ( 1H, dd), 2.86 ( 1H, bd), 4.21 ( 1H, m), 4.52 ( 1H, m), 4.93 (1H, bs), 4.98 (1H, bs), 5.82 (1H, d, J 11.6), 6.45 (1H,d, J 11.6).

Preparation 15

Compound 107j

The compound was prepared using the method of Preparation 14, except that the Grignard reagent was prepared from Compound 14 (5.9 g). 107j: $\delta$ (300 MHz) 0.05 (12H, bs), 0.08 (9H, s), 0.53 (3H, s), 0.80 (9H, m), 0.86 (9H, bs), 0.89 (9H, bs), [1.05–2.05 (26H, m, including 1.43 (4H, q)], 2.30 (1H, m), 2.56 (1H, m), 2.86 (1H, m), 4.21 (1H, m), 4.52 (1H, m), 4.93 (1H, m), 4.98 (1H, m), 5.82 (1H, d, J 11.5), 6.45 (1H, d, J 11.5).

Preparation 16

Compound 108j

The compound was prepared using the method of Preparation 14, except that the Grignard reagent was prepared from Compound 16 (5.5 g).

Procedure 3

Preparation of Compounds VII from Aldehyde (1) and Side Chain Fragment B (Scheme 4)

A solution of lithium di-iso-propylamide (0.4M in THF-hexanes, 3:1) was added dropwise via a syringe (10 minutes) to a solution of the side chain fragment B in dry THF (8 ml), stirred at $-25°$ C. under nitrogen. The resulting yellow solution was then cooled to $-40°$ C., and a solution of the aldehyde (1) (1.21 g) in dry THF (8 ml) was added dropwise (5 minutes). After stirring for 30 minutes, benzoyl chloride (0.6 ml) was added dropwise, and the mixture was allowed to warm to 0° C. for a further 30 minutes. The reaction mixture was treated with ether (10 ml) and water (1 ml) and partitioned between ethyl acetate (100 ml) and water (50 ml). The organic layer was washed with brine, dried, and concentrated in vacuo to give a crude oil containing compound VI (Y=PhC(O)) as a mixture of diastereoisomers. This was dissolved in ethyl acetate (5 ml) and diluted with methanol (50 ml, saturated with and containing suspended disodium hydrogen phosphate). To the ice-cooled mixture was added sodium amalgam (ca. 5% Na, 15 g), and the reaction mixture was stirred at 5° C. under nitrogen for 15 hours. The mixture was then partitioned between ethyl acetate (200 ml) and water (200 ml) (decanting from the mercury), and the organic layer was washed with brine, dried and concentrated in vacuo. Purification of the residue by chromatography gave VII.

Preparation 17

Compounds 109j and 110j

This compound was prepared from 1j using Procedure 3 in which the side chain fragment B was compound 23 (0.66 g) and 12 ml of the lithium di-iso-propylamide solution was used. The intermediate VIj has $R^5$=OH. The chromatography was performed using 10% ethyl acetate in petroleum ether as eluant. The major product (more polar) 109j was recrystallized from Et$_2$O-MeOH. 109j; $\delta$ (300 MHz) 0.05 (12H, bs), 0.50 (3H, s), 0.85 (6H, t, J 7.5), 0.86 (9H, s), 0.89 (9H, s), 0.90 (3H, d, J 6.6), 1.1–2.1 (23H, m), 2.30 (1H, bd, J 14), 2.55 (1H, dd, J 14 and 5), 2.86 (1H, bd, J 12), 4.21 (1H, m), 4.53 (1H, m), 4.93 (1H, bs), 4.98 (1H, bs), 5.30 (2H, m), 5.80 (1H, d, J 12), and 6.45 (1H, d, J 12); $\lambda_{max}$ 270 nm. 110j; $\delta$ (300 MHz) 0.05 (12H, bs), 0.47 (3H, s), 0.85 (6H, t), 0.86 (9H, s), 0.89 (9H, s), 0.9 (3H, d), 1.1–2.1 (22H, m), 2.30 (1H, m), 2.35 (1H, m), 2.55 (1H, dd, J 14 and 5), 2.86 (1H, bd, J 12), 4.21 (1H, m), 4.53 (1H, m), 4.93 (1H, bs), 4.98 (1H, bs), 5.2 (2H, m), 5.80 (1H, d, J 12 ), and 6.45 ( 1H, d, J 12 ); $\lambda_{max}$ 270 nm.

Procedure 4

Preparation of Compound XIV from the Corresponding Compound XIII (Scheme 6)

A mixture of anthracene (0.10 g), triethylamine (20 mg), and the compound XIII (0.20 g) in toluene (15 ml), Stirred under an atmosphere of nitrogen in a Pyrex flask immersed in a water bath at 20° C., was illuminated with radiation from a high pressure Hg lamp (type: Hanau TQ 718Z2) for 30 minutes. The reaction mixture was filtered and concentrated in vacuo to give a residue. This was purified by chromatography (30 g silica gel) to give XIV.

Preparation 18

Compound 102k

The compound was prepared using Procedure 4 in which starting material XIII was compound 102j. (Eluant: toluene-acetone, 97:3) 102k; $\delta$ (300 MHz) 0.06 (12H, s), 0.15–0.38 (2H, m), 0.52 (3H, s), 0.40–0.57 (2H, m), 0.87 (18H, s), 0.94 (3H, d, J 7), 0.65–2.15 (16H, m), 2,20 (1H, dd), 2.44 (1H, dd), 2.80 (1H, bd), 3.44 (1H, t), 4.18 (1H, m), 4.36 (1H, m), 4.85 (1H, d, J 2), 5.17 (1H, m), 5.46 and 5.58 (each 1H, dd, J 16 and 9), 6.00 (1H, d, J 11), 6.22 (1H, d, J 11); $\lambda_{max}$ 265 nm.

Preparation 19

Compound 103k

The compound was prepared using Procedure 4 in which starting material XIII was compound 103j. (Eluant: toluene-acetone 97:3) 103k; $\delta$ (300 MHz) 0.06 (12H, s), 0.15–0.38 (2H, m), 0.52 (3H, s), 0.40–0.57 (2H, m), 0.87 (18H, s), 0.94 (3H, d, J 7), 0.65–2.15 (16H, m), 2,20 (1H, dd), 2.44 (1H, dd), 2.80 (1H, bd), 3.38 (1H, t), 4.18 (1H, m), 4.36 (1H, m), 4.85 (1H, d, J 2), 5.17 (1H, m), 5.48 (2H, m), 6.00 (1H, d, J 11 ), 6.22 (1H, d, J 11 ); $\lambda_{max}$ 265 nm.

Preparation 20

Compound 106k

The compound was prepared using Procedure 4 in which starting material XIII was compound 106j. (Eluant: petroleum ether to 2% ether in petroleum ether) 106k; $\delta$ (300 MHz) 0.05 (12H, bs), 0.09 (9H, s), 0.52 (3H, s), 0.83 (3H, d, J 6), 0.88 (18H, s), 1.1–2.05 (26H, m, including 1.19 (6H, s)), 2.20 (1H, dd, J 13 and 7), 2.43 (1H, dd, J and 4), 2.81 (1H, m) 4.18 (1H, m), 4.36 (1H, m), 4.86 (1H, bd), 5.17 (1H, bd), 6.01 (1H, d, J 11), 6.22 (1H, d, J 11); $\lambda_{max}$ 265 nm.

Preparation 21

Compound 107k

The compound was prepared using Procedure 4 in which starting material XIII was compound 107j. (Eluant: petroleum ether to 2% ether in petroleum ether) 107k; $\delta$ (300 MHz) 0.05 (12 H, bs), 0.08 (9H, s), 0.52 (3H, s), 0.80 (9H, m), 0.87 (18H, s), 1.05–2.0 (26H, m, including 1.43 (4H, q), 2.21 (1H, dd), 2.43 (1H, bd) 2.82 (1H, bd), 4.16 (1H, m), 4.37 (1H, m), 4.85 (1H, m), 5.17 (1H, m), 6.01 (1H, d, J 11), 6.23 (1H, d, J 11);$\lambda_{max}$ 265 nm.

Preparation 22

Compound 109k

The compound was prepared using Procedure 4 in which starting material XIII was compound 109j. (Eluant: 20% ether in petroleum ether).

Preparation 23

Compound 5

A stirred solution of 1j (3.9 g), and methoxycarbonyl-methylene-triphenylphosphorane (4.6 g) in toluene (40 ml) was heated under reflux for 3 hours. The reaction mixture was cooled, filtered, and concentrated in vacuo. Purification of the residue by chromatography (200 g silica gel; 5% ether in petroleum ether as eluant) followed by recrystalization from ether-methanol gave the title compound as needles; δ (300 MHz) 0.05 (12H, m), 0.49 (3H, s), 0.86 (9H, s), 0.89 (9H, s), 1.00 (3H, d), 1.03–2.05 (13H, m), 2.24 (1H, m), 2.31 (1H, bd), 2.54 (1H, dd), 2.85 (1H, dd), 3.73 (3H, s), 4.21 (1H, m), 4.52 (1H, m), 4.93 (1H, m), 4.97 (1H, m), 5.76 (1H, d, J 15.6), 5.80 (1H, d), 6.43 (1H, d), 6.88 (1H, dd, J 15.6 and 9.9).

Preparation 24

Compound 111j

To a stirred solution of 5 (3.3 g) in dry THF (35 ml) at −70° C. under $N_2$ was added di-isobutylaluminium hydride (1M solution in hexanes (15 ml) for compound 2; 8 ml for compound 3) dropwise. After stirring for 30 minutes, methanol (3 ml) was added dropwise, and the reaction mixture was allowed to warm up to room temperature. EtOAc and water were added, and after stirring for an additional 30 minutes, the organic phase was separated, washed with brine, dried and concentrated to give the title compound. δ (300 MHz) 0.05 (12H, m), 0.51 (3H, s), 0.86 (9H, s), 0.89 (9H, s), 0.94 (3H, d), 1.00–2.20 (15H, m), 2.30 (1H, bd), 2.55 (1H, dd), 2.85 (1H, bd), 4.08 (2H, bs), 4.21 (1H, m), 4.52 (1H, m), 4.93 (1H, m), 4.97 (1H, m), 5.56 (2H, m), 5.82 (1H, d), 6.44 (1H, d).

Preparation 25

Compound 2j

Pyridinium dichromate (0.5 g) was added at room temperature to a stirred solution of compound 111j (0.53 g) in dichloromethane (10 ml). After stirring for 3 hours the mixture was diluted with ether and filtered. The filtrate was concentrated in vacuo and purified by chromatography (silica gel, hexane:ether 4:1 as eluant) to give 2j; δ (300 MHz) 0.06 (12H, m), 0.50 (3H, s), 0.85 (9H, s), 0.89 (9H, s), 1.05 (3H, d), 1.06–2.10 (13H, m), 2.30 (1H, bd), 2.40 (1H, m), 2.54 (1H, dd), 2.86 (1H, bd), 4.21 (1H, m), 4.52 (1H, m), 4.93 (1H, m), 4.97 (1H, m), 5.81 (1H, d), 6.06 (1H, dd, J 15.6 and 7.9), 6.43 (1H, d), 6.76 (1H, dd, J 15.6 and 9.8), 9.52 (1H, d, J 7.9).

Preparation 26

1(S),3(R)-bis-tert-butyldimethylsilyloxy-20(R)-phenyl-thiomethyl-9,10-secopregna-5(E),7(E),10(19)-triene A solution of potassium thiophenoxide in DMF [prepared by adding potassium tert-butoxide (0.35 g) to thiophenol (0.35 g) dissolved in DMF (5 ml)] was added to a solution of 3j (1 g) in THF (5 ml). After 30 minutes, the reaction mixture was worked up (ether) and purified by chromatography (2% ether in petroleum ether as eluant) to give the title compound. δ (300 MHz) 0.05 (12H, m), 0.51 (3H, s), 0.86 (9H, s), 0.89 (9H, s), 1.04 (3H, d), 1.20–2.0 (13H, m), 2.04 (1H, bt), 2.30 (1H, bd), 2.54 (1H, dd), 2.75 (1H, dd), 2.85 (1H, bd), 3.24 (1H, dd), 4.21 (1H, m), 4.52 (1H, m), 4.93 (1H, bs), 4.97 (1H, bs), 5.71 (1H, d), 6.44 (1H, d), 7.10–7.4 (5H, m).

Preparation 27

1(S),3(R)-bis-tert-butyldimethylsilyloxy-20(R)-phenyl-sulphonylmethyl-9,10-secopregna-5(E),7(E),10(19)-triene (Compound 4j)

To a solution of 1(S),3(R)-bis-tert-butyldimethyl-silyloxy-20(R)-phenylthiomethyl-9,10-secopregna-5(E),7(E),-10(19)-triene (Preparation 26) (0.9 g) in ethyl acetate (8 ml) and ethanol (15 ml) was added sodium hydrogen carbonate (0.5 g), aqueous sodium tungstate (3%, 0.5 ml) and hydrogen peroxide (30%, 2 ml). The stirred mixture was heated at 60° C. for 8 hours, cooled and worked-up (ethyl acetate). Purification by chromatography (40% ether in petroleum ether as eluant) gave 4j. δ (300 MHz) 0.05 (12H, m), 0.36 (3H, s), 0.86 (9H, s), 0.89 (9H, s), 1.10 (3H, d), 1.5–2.15 (m, 13H), 2.29 (1H, bd), 2.52 (1H, dd), 2.83 (1H, bd), 2.86 (1H, dd), 3.43 (1H, dd), 4.20 (1H, m), 4.51 (1H, m), 4.93 (1H, m), 4.96 (1H, m), 5.78 (1H, d), 6.41 (1H, d), 7.57 (3H, m), 7.92 (2H, m).

Preparation 28, 29, and 30

Compounds 2k, 3k, and 4j

Each compound was prepared analogously to Procedure 4 in which the starting material was the corresponding compound j. The eluant used was that used in the purification of the compound j.

Preparation 31

Compounds 112j and 113j

Using Procedure 2(b) as follows: To a solution of Compound 1j (0.8 g) in dry THF (7 ml), cooled to −40° C. and stirred under $N_2$, was added dropwise a solution of methyl-lithium (1.5M in ether, 1.2 ml). After 15 minutes, ether (50 ml) was added and the reaction mixture was worked up. The residue was purified by chromatography (10% ethyl acetate in petroleum ether as eluant) to give the less polar isomer (isomer A) 112j; NMR: δ=0.05 (m, 12H), 0.54 (s, 3H), 0.85 (d, 3H), 0.86 (s, 9H), 0.89 (s, 9H), 1.13 (d, 3H, J=6.3), 1.00–2.10 (m, 15H), 2.31 (bd, 1H), 2.54 (dd, 1H), 2.88 (bd, 1H), 4.06 (m, 1H), 4.21 (m, 1H), 4.52 (m, 1H), 4.93 (m, 1H), 4.98 (m, 1H), 5.82 (d, 1H, J=11.4), 6.44 (d, 1H, J=11.4), and the more polar isomer 113j (isomer B); NMR: δ=0.05 (m, 12H), 0.56 (s, 3H), 0.86 (d, 3H), 0.86 (s, 9H), 0.89 (s, 9H), 1.07 (d, 3H, J=6.3), 1.00–2.10 (m, 15H), 2.31 (bd, 1H), 2.54 (dd, 1H), 2.88 (bd, 1H), 4.10 (m, 1H),4.2! (m, 1H), 4.:52 (m, 1H), 4.93(m, 1H), 4.98 (m, 1H), 5.82 (d, 1H, J=11.4), 6.44 (d, 1H, J=1.4).

Preparation 32

Compound 114j and 115j

Using Procedure 2a, starting with compounds 19 and 1j, and using 5% ethyl acetate in petroleum ether as eluant for the chromatography, the title compounds were obtained. Major isomer (114j); δ (300 MHz) 0.05 (12H, m), 0.08 (9H, s), 0.54 (3H, s), 0.83 (3H, d), 0.86 (9H, s), 0.89 (9H, s), 1.18 (6H, s), 1.00–2.12 (23H, m), 2.31 (1H, bd), 2.55 (1H, dd) 2.88 (1H, bd), 3.85 (1H, m), 4.21 (1H, m), 4.53 (1H, m), 4.93 (1H, m), 4.98 (1H, m), 5.83 (1H, d), and 6.45 (1H, m). The minor isomer (115j) was the more polar isomer, δ (300 MHz ) in agreement with assigned structure.

Preparation 33

Compounds 116j and 117j

These compounds were prepared from 1j using procedure 3 in which the side chain fragment B was compound 29 (0.6 g) and 12 ml of the lithium di-iso-propylamide solution was used. The intermediate VIj has $R^5$=OH. The chromatography was performed using 10% ethyl acetate in petroleum ether as eluant to give the less polar 22Z isomer (117j); δ (300 MHz) 0.05 (12H, m), 0.47 (3H, s), 0.86 (9H, s), 0.89 (9H, s), 0.91 (3H, d), 0.97 (3H, d), 1.15 (3H, s), 1.18 (3H, s), 1.07–2.20 (14H, m), 2.31 (1H, bd), 2.39 (1H, m), 2.54 (2H, m), 2.85 (1H, bd), 4.21 (1H, m), 4.52 (1H, m), 4.92 (1H, m), 4.97 (1H, m), 5.07 (1H, t, J 10.9), 5.35 (1H, t, J 10.9), 5.81 (1H, d), and 6.45 (1H, d); $\lambda_{max}$ 270 nm; and the more polar 22E isomer (116/); δ (300 MHz) 0.05 (12H, m), 0.51 (3H, s), 0.86 (9H, s), 0.89 (9H, s), 0.93 (3H, d), 0.99 (3H, d), 1.13 (3H, s), 1.16 (3H, s), 1.05–2.22 (16H, m), 2.30 (1H, bd), 2.54 (1H, dd), 2.85 (1H, bd), 4.21 (1H, m), 4.52 (1H, m), 4.92 (1H, m), 4.97 (1H, m), 5.40 (2H, m), 5.81 (1H, d), and 6.44 (1H, d).

Preparation 34

Compounds 118j and 119j

This compound was prepared from 1j using procedure 3 in which the side chain fragment B was compound 28 (0.6 g) and 12 ml of the lithium di-iso-propylamide solution was used. The intermediate VIj has $R^5$=OH. The chromatography was performed using 10% ethyl acetate in petroleum ether as eluant to give the 22Z isomer (119j) and the 22E isomer (118j).

Preparation 35–47

Compounds 104k, 105k, 108k, 110k, 111k, 112k, 113k, 114k, 115k, 116k, 117k, 118k and 119k.

Each compound was prepared using Procedure 4 in which the starting material XIII was the corresponding compound j. (Eluant: the same eluant as used in the preparation of the corresponding compound j).

Preparation 48

1(S),3(R)-bis-tert-butyldimethylsilyloxy-20(R)-p-toluenesulphonyloxymethyl-9,10-secopregna-5(Z),7(E), 10(19)-triene (Compound 3k)

The compound was prepared analogously to Procedure 4 in which the starting material was 3j. 5% Ether in petroleum ether was used as eluant.

Preparation 49

1(S),3(R)-bis-tert-butyldimethylsilyloxy-20(R)-phenylsulphonylmethyl-9,10-secopregna-5(Z),7(E),10(19)-triene (Compound 4k)

The compound was prepared analogously to Procedure 4 in which the starting material was 4j. 40% Ether in petroleum ether was used as eluant.

Preparation 50

1(S),3(R)-bis-tert-butyldimethylsilyloxy-20(R)-hydroxymethyl-9,10-secopregna-5(Z),7(E),10(19)-triene The compound was prepared analogously to Procedure 4 in which the starting material was 1(S),3(R)-bis-tert-butyldimethylsilyloxy-20(R)-hydroxymethyl-9,10-secopregna-5(E),7(E),10(19)-triene (Preparation 9). 40% Ether in petroleum ether was used as eluant.

Preparation 51

1(S),3(R)-bis-tert-butyldimethylsilyloxy-20(S)-(4-methyl-1-pentyl)-9,10-secopregna-5(Z),7(E),10(19)-triene The stirred Grignard reagent obtained from isoamyl bromide (3.0 g) and magnesium (0.53 g) in dry THF (15 ml) was treated at 0° C. with a solution of lithium chloride (68 mg) and anhydrous cupric chloride (108 mg) in dry THF (8 ml) followed by a solution of Compound 3k (1.0 g) in dry THF (5 ml). After 5 hours, the reaction mixture was partitioned between water and ether, and the ether layer was washed with brine, dried and concentrated in vacuo. Purification of the residue by chromatography (150 g silica gel, petroleum ether to 2% ether in petroleum ether as eluant) gave the title compound; δ (300 MHz) in agreement with assigned structure.

Procedure 5

Preparation of Compound I from the Corresponding Compound XIV (Scheme 6)

A solution of the compound XIV (0.2 g) and tetra-n-butylammonium fluoride trihydrate (0.4 g) in THF (10 ml) was heated at 60° C. under an atmosphere of nitrogen for 50 minutes. After cooling, the reaction solution was partitioned between ethyl acetate (40 ml) and 2% sodium hydrogen carbonate solution (30 ml), and the organic layer was washed with water and brine, dried and concentrated. The residue was purified by chromatography (30 g silica gel, ethyl acetate as eluant) to give I.

The compounds of Examples 1 to 18 were prepared using procedure 5 in which starting material XIV was respectively compounds 102k, 103k, 106k, 107k, 109k, 110k, 111k, 112k, 113k, 104k, 105k, 114k, 115k, 108k, 116k, 117k, 118k, and 119k.

The starting material for Example 19 was the compound of Preparation 51. All exemplified compounds showed $\lambda_{max}$ (EtOH) 264–265 nm.

Example 1

20(S)-(3'-Cyclopropyl-3'-hydroxyprop-1'(E)-enyl)-1(S),3(R)-Dihydroxy-9,10-secopregna-5(Z),7(E),10(19)-triene (Isomer A) (Compound 120)

δ (300 MHz) 0.15–0.36 (2H, m), 0.40–0.60 (2H, m), 0.51 (3H, s), 0.92 (3H, m, J 6.6), 0.80–2.15 (18H, m), 2.29 (1H, dd), 2.57 (1H, dd), 2.79 (1H, dd), 3.43 (1H, t), 4.20 (1H, m), 4.41 (1H, m), 4.98 (1H, m), 5.31 (1H, m), 5.45 (1H, dd, J 15.5 and 6), 5.56 (1H, dd, J 15.5 and 9), 5.99 (1H, d, J and 6.35 (1H, d, J 11 ).

Example 2

20(S)-(3'-Cyclopropyl-3'-hydroxyprop-1'(E)-enyl)-1(S),3(R)-Dihydroxy-9,10-secopregna-5(Z),7(E),10(19)-triene (Isomer B) (Compound 121)

δ (300 MHz) 0.15–0.40 (2H, m), 0.41–0.60 (2H, m), 0.53 (3H, s), 0.95 (3H, m, J 6.6), 0.80–2.15 (18H, m), 2.31 (1H, dd), 2.60 (1H, dd), 2.81 (1H, dd), 3.40 (1H, m), 4.23 (1H, m), 4.43 (1H, m), 5.00 (1H, m), 5.33 (1H, m), 5.50 (1H, m), 6.01 (1H, d, J 11), and 6.37 (1H, d, J 11).

Example 3

1(S),3(R)-Dihydroxy-20(S)-(4-hydroxy-4-methyl-1-pentyl)-9,10-secopregna-5(Z),7(E), 10(19)-triene (Compound 122)

δ (300 MHz) 0.53 (3H, s), 0.83 (6H, t, J 6),1.1–2.1 (29H, m, including 1.20 (6H, s)), 2.30 (1H, dd), 2.58 (1H, bd), 2.81 (1H, bd), 4.22 (1H, m), 4.42 (1H, m), 4.99 (1H, bs), 5.32 (1H, bs), 6.00 (1H, d, J 11), 6.36 (1H, d, J 11).

Example 4

1(S),3(R)-Dihydroxy-20(S)-(5-ethyl-5-hydroxy-1-heptyl)-9,10-secopregna-5(Z),7(E),10(19)-triene (Compound 123)

δ (300 MHz) 0.54 (3H, s), 0.82 (3H,d), 0.84 (6H, t), 1.0–2.0 [29H, m, including 1.47 (4H, q)], 2.31 (1H, m), 2.59 (1H, bd), 2.83 (1H, bd), 4.23 (1H, m),) 4.43 (1H, m), 5.00 (1H, bs), 5.32 (1H, bs), 6.01 (1H, d, J 11) and 6.38 (1H, d, J 11).

Example 5

1(S), 3(R)-Dihydroxy-20(S)-(5-ethyl-5-hydroxy-hept-1(E)-en-1-yl)-9,10-secopregna-5(Z),7(E), 10(19)-triene (Compound 124)

δ (300 MHz) 0.51 (3H, s), 0.85 (6H, t), 0.91 (3H, d), 1.1–2.2 [25H, m, including 1.47 (4H, q)], 2.31 (1H, m), 2.59 (1H, bd), 2.82 (1H, bd), 4.23 (1H, m),) 4.43 (1H, m), 4.99 (1H, bs), 5.30 (2H, m), 5.33 (1H, bs), 6.02 (1H, d, J 11) and 6.37 (1H, d, J 11).

Example 6

1(S),3(R)-Dihydroxy-20(S)-(5-ethyl-5-hydroxy-hept-1(Z)-en-l-yl )-9,10-secopregna-5(Z), 7(E),10(19)-triene (Compound 125)

δ (300 MHz) in agreement with assigned structure.

Example 7

1(S),3(R)-Dihydroxy-20(S)-(3-hydroxyprop-1(E)-enyl)-9,10-secopregna-5(Z),7(E),10(19)-triene (Compound 126)

δ (300 MHz) in agreement with assigned structure.

Example 8

1(S),3(R)-Dihydroxy-20(R)-(1-hydroxy-1-ethyl)-9,10-secopregna-5(Z),7(E)9,10(19)-triene (Isomer A) (Compound 127)

δ (300 MHz) in agreement with assigned structure.

Example 9

1(S),3(R)-Dihydroxy-20(R)-(1-hydroxy-1-ethyl)-9,10-secopregna-5(Z),7(E),10(19)-triene (Isomer B) (Compound 128)

δ (300 MHz ) in agreement with assigned structure.

Example 10

1(S),3(R)-Dihydroxy-20(R)-(1,4-dihydroxy-4-methyl-1-pentyl)-9,10-secopregna-5(Z),7(E),10(19)-triene (Isomer A) (Compound 129)

δ (300 MHz) in agreement with assigned structure.

Example 11

1(S),3(R)-Dihydroxy-20(R)-(1,4-dihydroxy-4-methyl-1-pentyl)-9,10-secopregna-5(Z), 7 (E),10(19)-triene (Isomer B) (Compound 130)

δ (300 MHz ) in agreement with assigned structure.

Example 12

1(S),3(R)-Dihydroxy-20(R)-(1,6-dihydroxy-6-methyl-1-heptyl)-9,10-secopregna-5(Z), 7(E), 10(19)-triene (Isomer A) (Compound 131)

δ (300 MHz ) 0.55 (3H, s), 0.83 (3H, d ), 1.20 (6H, s), 1.20–2.10 (26H, m), 2.31 (1H, dd), 2.57 (1H, dd), 2.83 (1H, dd), 3.84 (1H, m), 4.22 (1H, m), 4.43 (1H, m), 4.99 (1H, bs), 5.33 (1H, bs), 6.02 (1H, d), 6.37 (1H, d).

Example 13

1(S),3(R)-Dihydroxy-20(R)-(1,6-dihydroxy-6-methyl-1-heptyl)-9,10-secopregna-5(Z),7 (E), 10(19)-triene (Isomer B) (Compound 132)

δ (300 MHz) 0.56 (3H, s), 0.85 (3H, d), 1.21 (6H, s), 1.20–2.10 (26H, m), 2.31 (1H, dd), 2.57 (1H, dd), 2.83 (1H, dd), 3.78 (1H, m), 4.22 (1H, m), 4.43 (1H, m), 4.99 (1H, bs), 5.33 (1H, bs), 6.02 (1H, d), 6.37 (1H, d).

Example 14

1(S),3(R)-Dihydroxy-20(S)-(6-hydroxy-6-methyl-1-heptyl) -9,10-secopregna-5(Z), 7(E), 10(19)-triene (Compound 133)

δ (300 MHz ) in agreement with assigned structure.

Example 15

1(S),3(R)-Dihydroxy-20(S)-(4-hydroxy-3(S), 4-dimethylpent-1(E)-enyl-9,10-secopregna-5(Z), 7(E), 10(19)-triene (Compound 134)

δ (300 MHz)0.50 (3H, s), 0.91 (3H, d), 0.97 (3H, d), 1.13 (3H, s), 1.15 (3H, s), 1.15–2.20 (18H, m), 2.29 (1H, dd), 2.57 (1H, dd), 2.79 (1H, bd), 4.20 (1H, m), 4.40 (1H, m), 4.98 (1H, bs), 5.31 (1H, bs), 5.38 (2H, m), 5.98 (1H, d), 6.35 (1H, d).

Example 16

1(S),3(R)-Dihydroxy-20(S)-(4-hydroxy-3(S),4-dimethylpent-1(Z)-enyl-9,10-secopregna-5(Z), 7(E), 10(19)-triene (Compound 135)

δ (300 MHz) 0.36 (3H, s), 0.91 (3H, d), 0.97 (3H, d), 0.97 (3H, d), 1.2–2.65 (20H, m). 2.82 (1H, bd), 4.23 (1H, m), 4.41 (1H, m), 5.00 (1H, s), 5.08 (1H, t), 5.33 (1H, s), 5.36 (1H, t), 6.01 (1H, d), 6.37 (1H, d), 1.15 (3H, s), 1.24 (3H, s).

Example 17

1(S),3(R)-Dihydroxy-20(S)-(4-hydroxy-3(R),4-dimethylpent-1(E)-enyl-9,10-secopregna-5(Z), 7(E), 10(19)-triene (Compound 136)

δ (300 MHz) in agreement with assigned structure.

Example 18

1(S),3(R)-Dihydroxy-20(S)-(4-hydroxy-3(R),4 -dimethylpent-1(Z) -enyl-9,10-secopregna-5(Z),7(E), 10(19)-triene (Compound 137)

δ (300 MHz) in agreement with assigned structure.

Example 19

1(S),3(R)-Dihydroxy-20(S)-(4-methyl-1-pentyl -9,10-secopregna-5(Z), 7(E), 10(19)-triene (Compound 138)

δ (300 MHz ) in agreement with assigned structure.

Example 20

Dermatological Cream Containing Compound 122

In 1 g almond oil was dissolved 0.1 mg 122. To this solution was added 40 g of mineral oil and 20 g of self-emulsifying beeswax. The mixture was heated to liquify. After the addition of 40 ml hot water, the mixture was mixed well. The resulting cream contains approximately 1 μg of 122 per gram of cream.

Example 21

Capsules containing Compound 122

122 was suspended in arachis oil to a final concentration of 5 μg 122/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100

μl of the 122 in oil suspension, such that each capsule contained 0.5 μg 122.

What we claim is:

1. A compound of the formula I

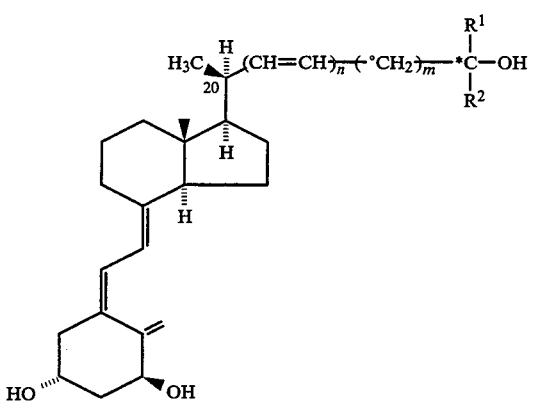

in which formula, n is 0 or 1, m is 0 or an integer from 1–7, $R^1$ and $R^2$, which may be the same or different, stand for hydrogen or $C_1$–$C_8$-hydrocarbyl, hydrocarbyl indicating the residue after removal of a hydrogen atom from a straight, branched or cyclic saturated or unsaturated hydrocarbon, or, taken together with the carbon bearing the hydroxyl group (starred in formula I), $R^1$ and $R^2$ form a saturated or unsaturated $C_3$–$C_8$ carbocyclic ring; and in addition, $R^1$ and/or $R^2$ and/or one of the m carbons designated by the "°" are optionally substituted with a hydroxyl group or one or more chlorine or fluorine atom(s); and finally one of the carbons designated "°" are optionally substituted by one or two $C_1$–$C_2$ alkyl group(s); and prodrugs and derivatives of the compounds of formula I in which one or more hydroxy groups have been transformed into —O-acyl or —O-glycosyl or phosphate ester groups; such masked groups being hydrolyzable in vivo. prodrugs thereof.

2. A diastereoisomer of a compound according to claim 1, in pure form; or a mixture of diastereoisomers of a compound according to claim 1.

3. A compound according to claim 1 which are selected from the group consisting of
1(S),3(R)-Dihydroxy-20(S)-(4-hydroxy-4-methyl-1-pent-yl)-9,10-secopregna-(5Z ), 7(E), 10(19)-triene
1(S),3(R)-Dihydroxy-20(S)-(5-ethyl-5-hydroxy-1-hept-yl)-9,10-secopregna-5(Z), 7 (E), 10(19)-triene
1(S),3(R)-Dihydroxy-20(S)-(5-ethyl-5-hydroxy-hept-1(E)-en-1-yl)-9,10-secopregna-5(Z),7(E),10(19)-triene.

4. A pharmaceutical composition containing an effective amount of one or more of the compounds of claim 1, together with a pharmaceutically acceptable, non-toxic carrier.

5. A pharmaceutical composition according to claim 4 for topical use containing from 0.1–100 μg/g of a compound of formula I.

6. A pharmaceutical composition according to claim 4 in dosage unit form.

7. A composition according to claim 6 containing from 0.025–100 μg for oral and parenteral formulations of a compound of formula I.

* * * * *

UNITED STATES PATENT AND TRADEMARK OFFICE
CERTIFICATE OF CORRECTION

PATENT NO. : 5,401,731

DATED : March 28, 1995

INVENTOR(S) : Martin J. Calverley
Ernst T. Binderup

It is certified that error appears in the above-identified patent and that said Letters Patent is hereby corrected as shown below:

Column 4, lines 50-65, change the formula

"

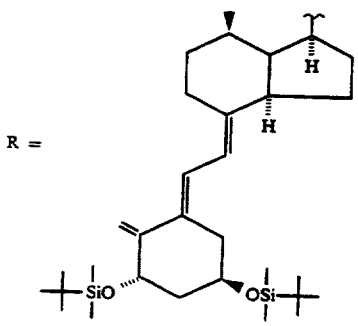

i or

"

to

UNITED STATES PATENT AND TRADEMARK OFFICE
CERTIFICATE OF CORRECTION

PATENT NO. : 5,401,731

DATED : March 28, 1995

INVENTOR(S) : Martin J. Calverley

Ernst T. Binderup

It is certified that error appears in the above-identified patent and that said Letters Patent is hereby corrected as shown below:

-- R =

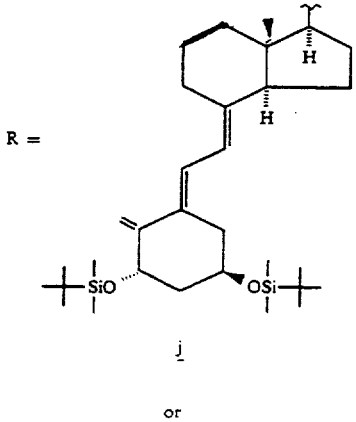

i or
--

UNITED STATES PATENT AND TRADEMARK OFFICE
CERTIFICATE OF CORRECTION

PATENT NO. : 5,401,731

DATED : March 28, 1995

INVENTOR(S) : Martin J. Calverley
Ernst T. Binderup

It is certified that error appears in the above-identified patent and that said Letters Patent is hereby corrected as shown below:

Column 5, lines 2-15, change the formula

"  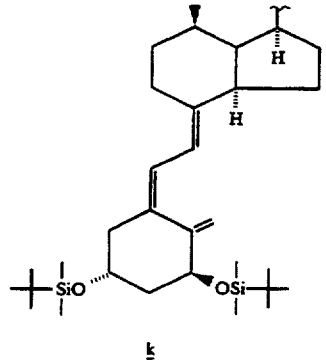  "

to

--  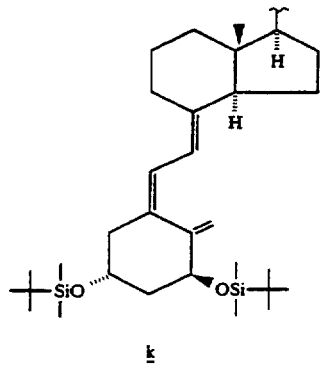  --

UNITED STATES PATENT AND TRADEMARK OFFICE
CERTIFICATE OF CORRECTION

PATENT NO. : 5,401,731

DATED : March 28, 1995

INVENTOR(S) : Martin J. Calverley
Ernst T. Binderup

It is certified that error appears in the above-identified patent and that said Letters Patent is hereby corrected as shown below:

Column 6, line 4, change the formula

"  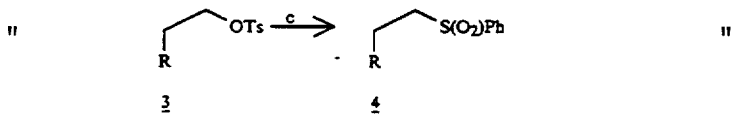  "

to

--  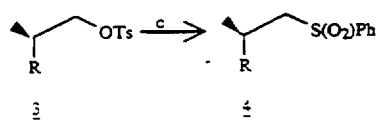  --

UNITED STATES PATENT AND TRADEMARK OFFICE
CERTIFICATE OF CORRECTION

PATENT NO. : 5,401,731
DATED : March 28, 1995
INVENTOR(S) : Martin J. Calverley, et al.

It is certified that error appears in the above-indentified patent and that said Letters Patent is hereby corrected as shown below:

Columns 5-6, following under Scheme 2, change

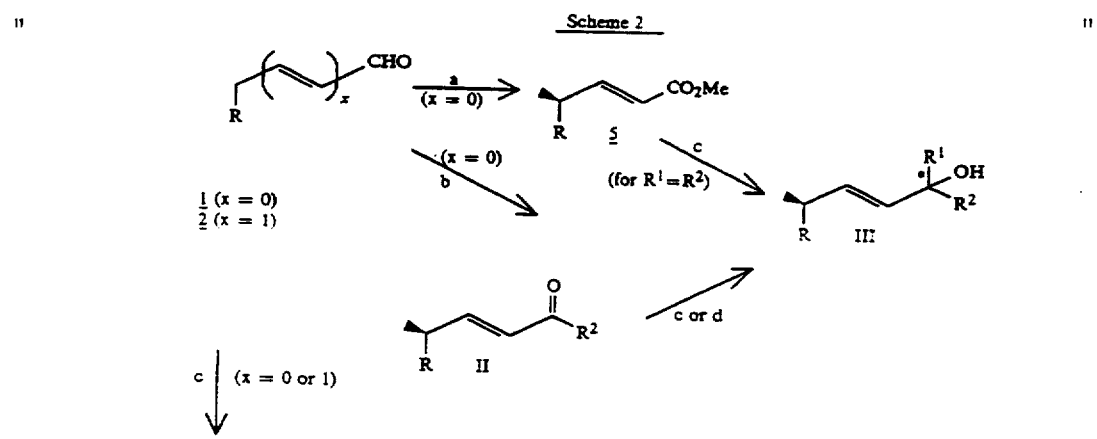

UNITED STATES PATENT AND TRADEMARK OFFICE
CERTIFICATE OF CORRECTION

PATENT NO. : 5,401,731                                    Page 6 of 12
DATED     : March 28, 1995
INVENTOR(S) : Martin J. Calverley, et al.

It is certified that error appears in the above-indentified patent and that said Letters Patent is hereby corrected as shown below:

to

-- 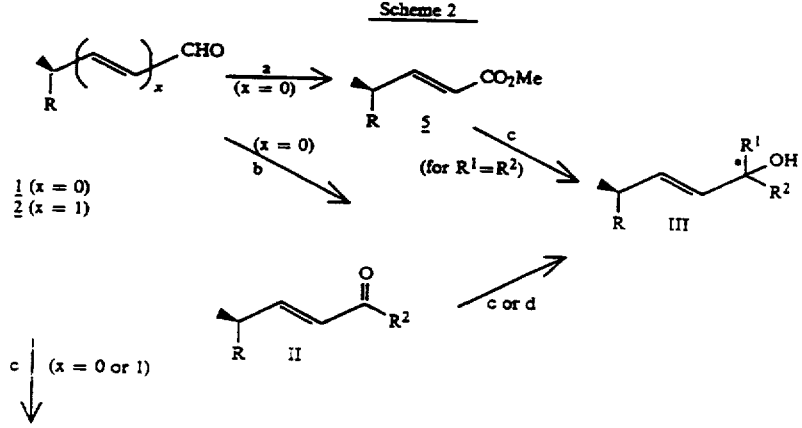 --

UNITED STATES PATENT AND TRADEMARK OFFICE
CERTIFICATE OF CORRECTION

PATENT NO. : 5,401,731
DATED : March 28, 1995
INVENTOR(S) : Martin J. Calverley, et al.

It is certified that error appears in the above-indentified patent and that said Letters Patent is hereby corrected as shown below:

Columns 5-6, preceding Notes to Scheme 2, change the formula

" 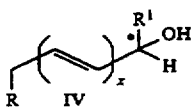 "

to

-- 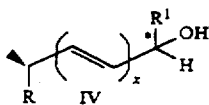 --

Column 7, line 1, change "Scheme 3" to --Scheme 4--.

UNITED STATES PATENT AND TRADEMARK OFFICE
CERTIFICATE OF CORRECTION

PATENT NO. : 5,401,731
DATED : March 28, 1995
INVENTOR(S) : Martin J. Calverley, et al.

It is certified that error appears in the above-indentified patent and that said Letters Patent is hereby corrected as shown below:

Columns 7-8, lines 2-8, change formula from

"
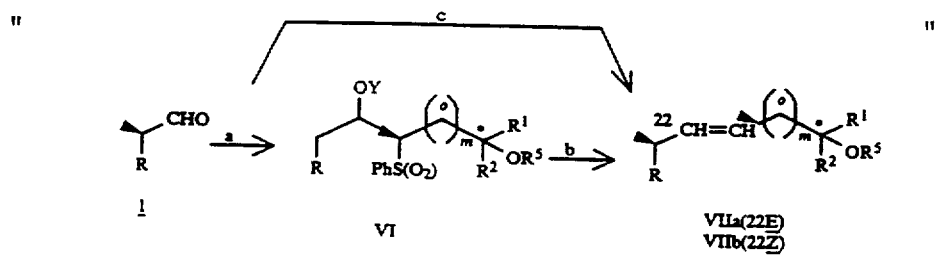
"

to

--
Scheme 4
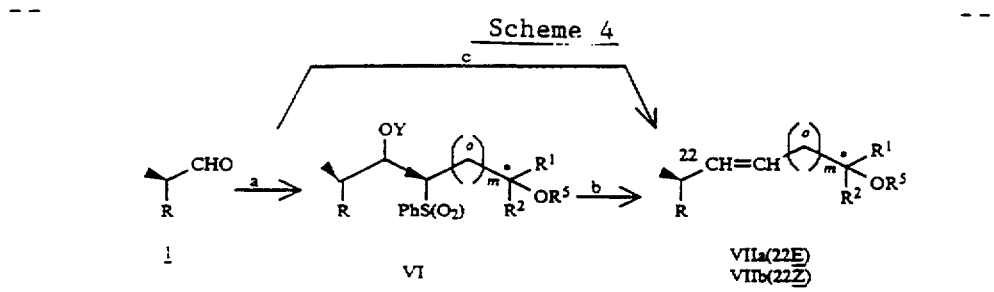
--

000
UNITED STATES PATENT AND TRADEMARK OFFICE
CERTIFICATE OF CORRECTION

PATENT NO. : 5,401,731  
DATED : March 28, 1995  
INVENTOR(S) : Ernst T. Binderup It is certified that error appears in the above-indentified patent and that said Letters Patent is hereby corrected as shown below:

Column 7, line 27, change the formula

"
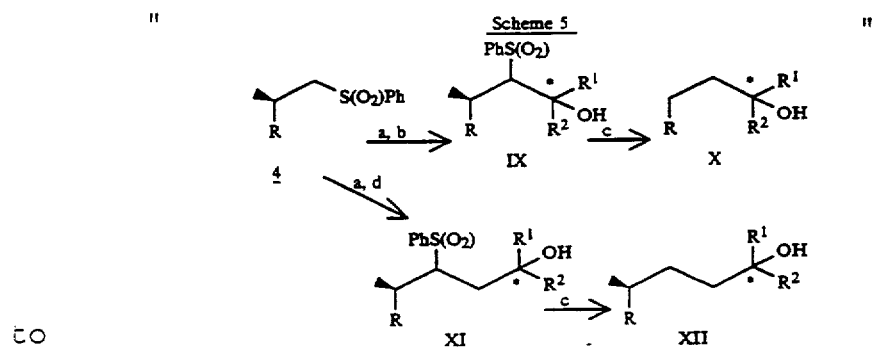
"

to

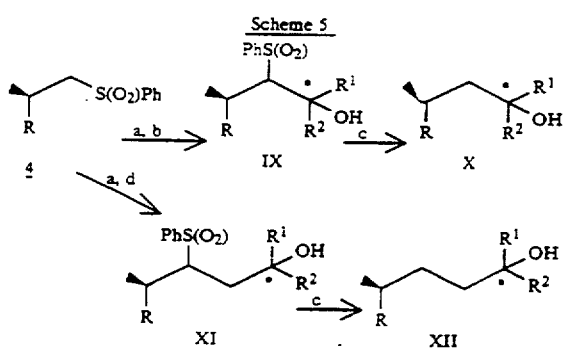

--

UNITED STATES PATENT AND TRADEMARK OFFICE
CERTIFICATE OF CORRECTION

PATENT NO. : 5,401,731

DATED : March 28, 1995

INVENTOR(S) : Martin J. Calverley
Ernst T. Binderup

It is certified that error appears in the above-identified patent and that said Letters Patent is hereby corrected as shown below:

Column 8, line 67, change "he" to --the--;

Column 11, line 57, start a new paragraph with "The present compounds are";

Column 20, line 3, center "Preparation 7a" over "Compound 31b";

Column 20, line 9, change "311" to ---31b---;

Column 20, line 20, change "6" to --- $\delta$ ---;

Column 21, line 14, change "1 K $\cancel{/}$" to --- 1 K $\delta$ ---;

Column 21, line 63, change " ($\xi$ = 24900)" to ---($\epsilon$ = 24900)---;

UNITED STATES PATENT AND TRADEMARK OFFICE
CERTIFICATE OF CORRECTION

PATENT NO. : 5,401,731
DATED : March 28, 1995
INVENTOR(S) : Ernst T. Binderup

It is certified that error appears in the above-indentified patent and that said Letters Patent is hereby corrected as shown below:

Column 9, lines 9-10, "Scheme 7" should read--

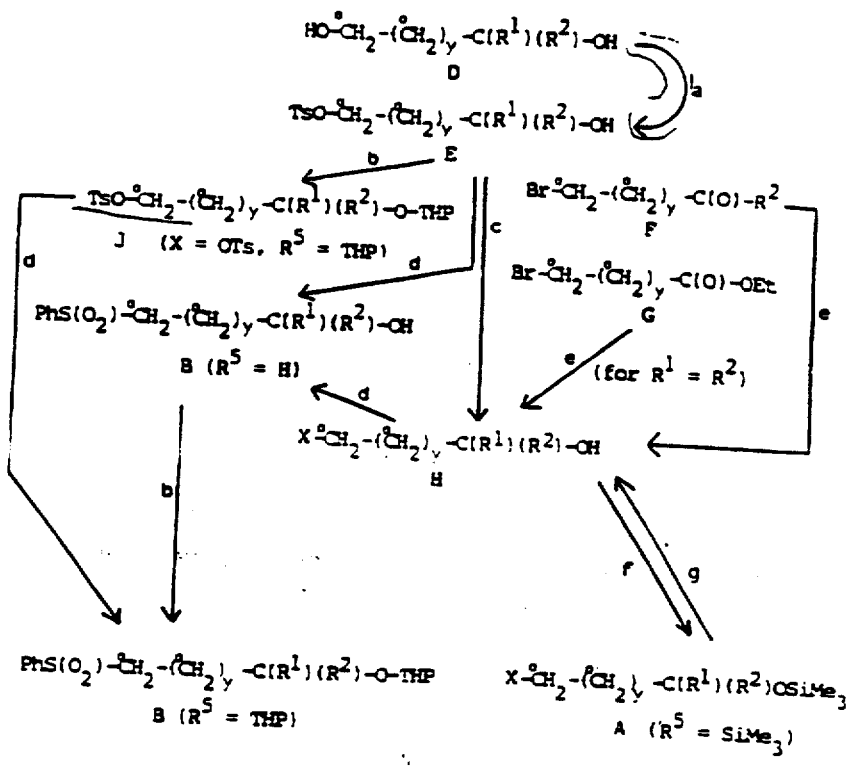

--.

UNITED STATES PATENT AND TRADEMARK OFFICE
CERTIFICATE OF CORRECTION

PATENT NO. : 5,401,731

DATED : March 28, 1995

INVENTOR(S) : Martin J. Calverley

Ernst T. Binderup

It is certified that error appears in the above-identified patent and that said Letters Patent is hereby corrected as shown below:

Column 22, line 2, change "($\xi$ = 24500)" to ---($\epsilon$ = 24500)---;

Column 26, line 40, change "4.2!" to ---4.21---;

Column 27, line 6, change "(116/)" to ---(116j)---;

Column 32, line 7, delete "prodrugs thereof".

Signed and Sealed this

Seventh Day of November, 1995

Attest:

BRUCE LEHMAN

*Attesting Officer*        *Commissioner of Patents and Trademarks*